United States Patent [19]

Shih et al.

[11] Patent Number: 5,463,074
[45] Date of Patent: Oct. 31, 1995

[54] IMIDAZOLYL OR IMIDAZOYLALKYL SUBSTITUTED WITH A FOUR OR FIVE MEMBERED NITROGEN CONTAINING HETEROCYCLIC RING

[75] Inventors: Neng-Yang Shih, North Caldwell; Robert Aslanian, Rockaway; Andrew Lupo, Jr., Emerson; John J. Piwinski, Parsippany; Michael J. Green, Skillman; Ashit K. Ganguly, Upper Montclair, all of N.J.

[73] Assignee: Schering Corporation, Kenilworth, N.J.

[21] Appl. No.: 244,851

[22] PCT Filed: Dec. 17, 1992

[86] PCT No.: PCT/US92/10743

§ 371 Date: Jun. 15, 1994

§ 102(e) Date: Jun. 15, 1994

Related U.S. Application Data

[63] Continuation-in-part of Ser. No. 809,781, Dec. 18, 1991, abandoned.

[51] Int. Cl.$^6$ .................. C07D 401/06; C07D 403/06; C07D 409/06; A61K 31/415
[52] U.S. Cl. ........................................................ 548/314.7
[58] Field of Search .......................... 548/314.7; 514/397

[56] References Cited

U.S. PATENT DOCUMENTS

| | | | |
|---|---|---|---|
| 2,987,522 | 6/1961 | Shen | 548/314.7 X |
| 3,470,197 | 9/1969 | Van Dyke | 548/314.7 |
| 3,491,098 | 2/1970 | Archer | 544/360 |
| 4,011,238 | 3/1977 | Fontanella et al. | 548/314.7 |
| 4,259,345 | 3/1981 | Cross et al. | 514/397 |
| 4,273,782 | 6/1981 | Cross et al. | 514/397 |
| 4,404,382 | 9/1983 | Gall | 546/193 |
| 4,404,387 | 9/1983 | Gall | 544/360 |
| 4,416,895 | 11/1983 | Thorogood | 514/396 |
| 4,431,653 | 2/1984 | Wei et al. | 542/420 |

(List continued on next page.)

FOREIGN PATENT DOCUMENTS

| | | | |
|---|---|---|---|
| 0197840 | 10/1986 | European Pat. Off. | 514/397 |
| 0338939 | 4/1988 | European Pat. Off. | 514/397 |

OTHER PUBLICATIONS

West Jr. et al., Journal of Neurochemistry, vol. 55, No. 5, pp. 1612–1616 (1990).

(List continued on next page.)

*Primary Examiner*—Floyd D. Higel
*Attorney, Agent, or Firm*—Henry C. Jeanette; John J. Maitner; James R. Nelson

[57] ABSTRACT

Disclosed is a compound of Formula I:

$$\text{(I)}$$

or a pharmaceutically acceptable salt or solvate thereof.

Also disclosed are pharmaceutical compositions comprising a pharmaceutically acceptable carrier and an effective amount of a Compound of Formula I.

Further disclosed is a method of treating allergy (for example asthma), inflammation, hypertension, raised intraocular pressure (such as glaucoma)—i.e., a method of lowering intraocular pressure, sleeping disorders, states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula I to a patient in need of such treatment.

19 Claims, No Drawings

U.S. PATENT DOCUMENTS

| | | | |
|---|---|---|---|
| 4,581,370 | 4/1986 | Diamond et al. | 514/399 |
| 4,587,239 | 5/1986 | Regel et al. | 514/184 |
| 4,767,778 | 8/1988 | Arrang et al. | 514/397 |
| 4,925,851 | 5/1990 | Houlihan | 514/326 |
| 4,935,417 | 6/1990 | Pascal et al. | 514/218 |
| 5,010,075 | 4/1991 | Pascal et al. | 514/218 |
| 5,021,434 | 6/1991 | Strehlke et al. | 514/341 |
| 5,066,663 | 11/1991 | Hobbs | 514/326 |
| 5,071,859 | 12/1991 | Knudsen et al. | 514/326 |
| 5,091,428 | 2/1992 | Pascal et al. | 514/252 |
| 5,264,449 | 11/1993 | Albaugh | 514/397 |

Other Publications

West Jr. et al, Molecular Pharmacology, 38:610–613 (1990).
Korte et al., Biochemical and Biophysical Research Communications, vol. 168, No. 3, pp. 979–986 (1990).
Derwent Abstract 86–273706/42 For EP 0197 840 (1986).
Derwent Abstract 90–184730/24 For US 4925851 (1990).
Derwent Abstract 90–180087/24 For EP 372125 (1990).
Derwent Abstract 88–309195/44 For US 4935417 (1988).
Derwent Abstract 89–237742/33 For JP 1172383 (1989).
Appel, Current Neurology, vol. 6, pp. 289g 313–316, (1987), ("Alzheimer's Disease").
Chemical Abstracts 80(15): 82801a (1973). Schumack.
CA 98 (23): 194919y (1983) Tchissambou et al.
CA 96(17): 139642m (1982) Waterman et al.
CA 106(11): 84602r (1987) Arrang et al. IV.
CA 89(13): 109229v (1978) DeGraw et al.
CA 89 (23): 197598t (1978) Malesct.
CA 72 (17): 90459v (1970) and CA 69 (3): 10467w (1968) Archer (1968).
RN 80101–09–3 For CA 96 (1): 6760b (1982) Bagli et al.

IMIDAZOLYL OR IMIDAZOYLALKYL SUBSTITUTED WITH A FOUR OR FIVE MEMBERED NITROGEN CONTAINING HETEROCYCLIC RING

The present application is the U.S. national application corresponding to International Application No. PCT/US 92/10743, filed Dec. 17, 1992 and designating the United States, which PCT application is in turn a continuation-in-part of U.S. application Ser. No. 07/809,781, filed Dec. 18, 1991 and now abandoned the benefit of which applications are claimed pursuant to the provisions of 35 U.S.C. 120, 363 and 365 (C).

BACKGROUND $H_3$ receptor sites are known and are of current interest to those skilled in the art—for example, see: West, Jr. et al., "Biexponential Kinetics of (R)-α-[$^3$H]Methylhistamine Binding to the Rat Brain $H_3$ Histamine Receptor", Journal of Neurochemistry, Vol. 55, No. 5, pp. 1612–1616, 1990; West, Jr. et al., "identification of Two $H_3$-Histamine Receptor Subtypes", Molecular Pharmacology, 38:610–613; and Korte et al., "Characterization and Tissue Distribution of $H_3$ Histamine Receptors in Guinea Pigs by $N^\alpha$-Methylhistamine", Biochemical and Biophysical Research Communications, Vol. 168, No. 3, pp. 9079–986.

Arrang et al. in U.S. Pat. No. 4,767,778 (issued Aug. 30, 1988) disclose a pharmaceutical composition containing a histamine derivative of the formula:

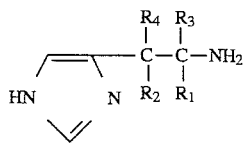

wherein each of $R_1$, $R_2$, and $R_4$, represents a hydrogen or a methyl, or $R_1$ and $R_2$ taken together represent a methylene, and $R_3$ is a hydrogen, a methyl or a carboxy, with the proviso that $R_1$, $R_2$, $R_3$, and $R_4$ are not simultaneously methyl groups. It is disclosed that the derivatives behave as complete agonists of the $H_3$ receptors in rat brain and produce a maximum inhibition of release identical to that induced by histamine (approximately 60%). It is also disclosed that the histamine derivatives powerfully inhibit the release and synthesis of histamine by very selectively stimulating the $H_3$ receptors. Consequently, according to Arrang et al., the derivatives are likely to decrease histaminergic transmission in the digestive tract and in the nervous, cardiovascular and immune systems. Arrang et al. disclose that the derivatives can be used in therapy as a drug having sedative effects, as a sleep regulator, anticonvulsant, regulator of hypothalamo-hypophyseal secretion, antidepressant, and modulator of cerebral circulation. According to Arrang et al., inhibition of the release of inflammation messengers in various allergic conditions (e.g., asthma) is expected to result from stimulation of the $H_3$ receptors of the lung. It is further disclosed that the inhibition of release of gastric histamine is likely to exert antisecretory and antiulcerative effects. According to Arrang et al., modification of release of the messengers of immune responses is likely to modulate the latter responses.

EP 0 338 939 discloses compounds of the formula:

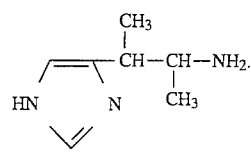

Derwent abstract 86-273706/42 for EP 0 197 840 discloses imidazole derivatives of the formula:

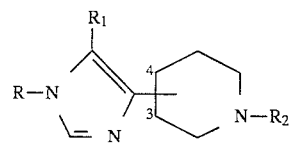

wherein $R_1$ is H, methyl or ethyl; R is H or $R_2$; and $R_2$ is 1–6C alkyl, piperonyl, 3-(benzimidazolon-1-yl)propyl, —CZ—$NHR_5$ or a group (i):

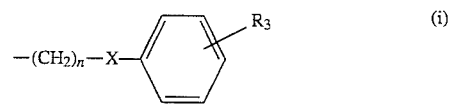

wherein n is 0—4; X is a bond, O, S, NH, CO, CH=CH or a group (ii):

$R_3$ is H, methyl, halo, CN, $CF_3$ or $COR_4$; $R_4$ is 1–6C alkyl, 3–6C cycloalkyl or phenyl (optionally substituted by methyl or F); Z is O, S, NH, N-methyl or N—CN; and $R_5$ is 1–8C alkyl, 3–6C cycloalkyl (optionally substituted by methyl, halo or $CF_3$), phenyl(1–3C)alkyl, naphthyl, adamantyl or p-toluenesulphonyl. It is disclosed that these compounds are phychotropic agents. It is also disclosed that these compounds antagonise the histamine H3 receptors and increase the speed of cerebral histamine renewal.

Derwent abstract 90-184730/24 for U.S. Pat. No. 4,925,851 discloses 2- or 4-(2-(1H-imidazol-1-yl)ethyl) piperidine compounds useful as antitumour agents for inhibiting lymphoma, sarcoma, myeloma and leukaemia. The compounds have the formula:

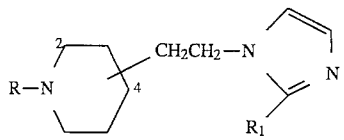

wherein R is —$CH_2(CH_2)_m$—Me, —CO—$(CH_2)_m$—Me or —CO—$CMe_2$—$R_2$; m is 2–18; $R_2$ is H or Me; $R_1$ is —$(CH_2)_n$—$R_3$; n is 0–13; $R_3$ is H, i-Pr or t-Bu; and the floating group is at the 2- or 4-position; with the proviso that (1) the sum of C atoms in $R_1$ does not exceed 13; and (2) the sum of C atoms in R and $R_1$ does not exceed 25.

Derwent abstract 90-180087/24 for EP 372125A discloses compounds of the formula:

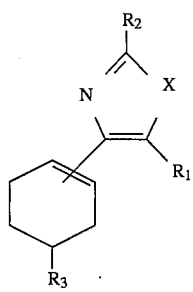

wherein X is O or S; $R_1$ is halo, $CF_3$, CN, $NO_2$, OH, or 1–6C alkoxy; $R_2$ is H, 1–6C alkyl, aryl, 7–13C aralkyl, optionally substituted amino or 5- or 6-membered N-containing ring; and $R_3$ is 1–6C hydrocarbyl, 7–13C aralkyl or 1–13C acyl. It is disclosed that these compounds have alpha2-antagonist activity with no dopamine activity and that they are useful for treating depression and other relates illnesses (e.g., anxiety or cognitive disorders).

Derwent abstract 88-309195/55 or U.S. Pat. No. 4,935,417 disclosed compounds of the formula:

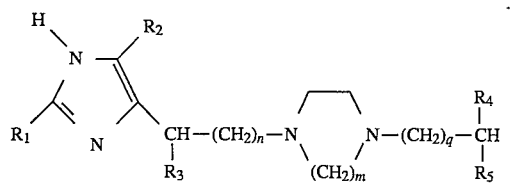

wherein (according to U.S. Pat. No. 4,935,417) $R^1$ is aryl, lower alkyl, cycloalkl or hydrogen; $R^2$ is aryl, lower alkyl or hydrogen; $R^3$ is lower alkyl, hydroxy or hydrogen; $R^4$ is aryl or hydrogen; $R^5$ is aryl or hydrogen; m is two or three; n is zero, one or two, provided that when $R^3$ is hydroxy, n is one or two; and q is zero, one, two or three. U.S. Pat. No. 4,935,417 discloses that these compounds are calcium channel antagonists useful for treating mammals having a variety of disease states, such as stroke, epilepsy, hypertension, angina, migraine, arrhythmia, thrombosis, embolism and also for treating of spiral injuries.

Compounds known in the art include:

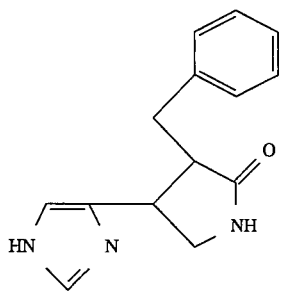

RN 85651-90-7
CA98(23):194919y (1)

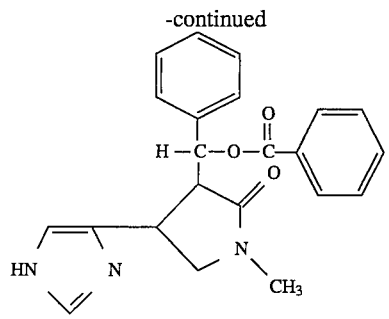

RN 81345-39-3
CA96(17):139642m (2)

and

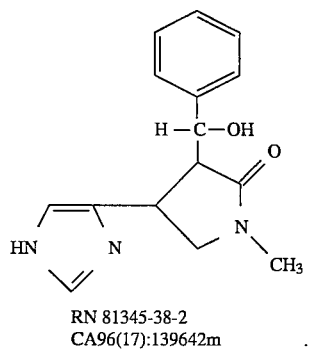

RN 81345-38-2
CA96(17):139642m (3)

Known compounds in the art also include compounds of the formula:

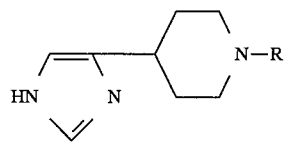

wherein R (Table 1) is:

TABLE 1

| NO. | R | RN | CA |
|---|---|---|---|
| 1 | —$CH_3$ | 106243-44-1 | 106(11):84602r |
| 2 | —$CH(CH_3)2$ | 106243-45-2 | 106(11):84602r |
| 3 | H | 106243-23-6 | 106(11):84602r |
| 4 | —$C(S)NHC(CH_3)_2CH_2C(H_3)$ | 106243-93-0 | 106(11):84602r |
| 5 | —$C(O)NHCH(CH_3)$(phenyl) | 106243-90-7 | — |
| 6 | —C(S)NH(p-chlorophenyl) | 106243-85-0 | — |
| 7 | —C(O)NH(phenyl) | 106243-77-0 | — |
| 8 | —$C(NH)N(CH_3)$(cyclopropyl) | 106243-73-6 | — |
| 9 | —$C(S)NHCH_3$ | 106243-61-2 | — |
| 10 | —$CH_2CH_2$-phenyl | 106243-49-6 | — |
| 11 | —$CH_2CH_2$-p-flurophenyl | 106243- | |

TABLE 1-continued

| NO. | R | RN | CA |
|---|---|---|---|
| 12 | benzyl | 67-8 106243-25-8 | — |

Additionally known compounds include:

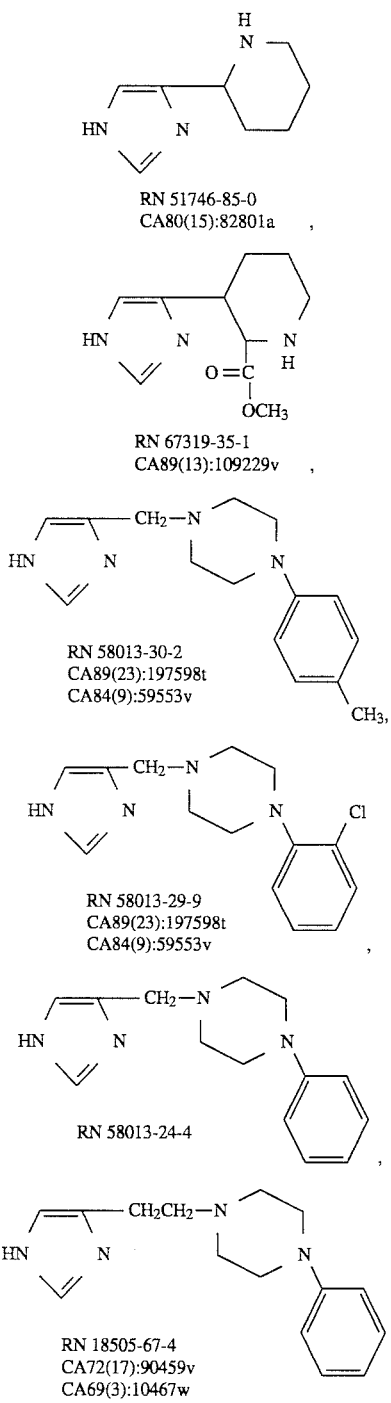

(1) RN 51746-85-0 CA80(15):82801a, (2) RN 67319-35-1 CA89(13):109229v, (3) RN 58013-30-2 CA89(23):197598t CA84(9):59553v, (4) RN 58013-29-9 CA89(23):197598t CA84(9):59553v, (5) RN 58013-24-4, (6) RN 18505-67-4 CA72(17):90459v CA69(3):10467w,

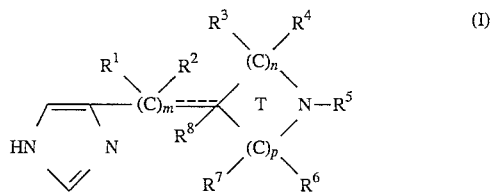

(7) RN 46906-54-1, (8) RN 46995-90-8 and (9) RN 80101-09-3 CA96(1):6760b

In view of the art's interest in compounds which effect the $H_3$ receptors, novel compounds having agonist or antagonist activity on $H_3$ receptors would be a welcome contribution to the art. This invention provides just such a contribution by providing novel compounds having $H_3$ agonist or antagonist activity.

SUMMARY OF THE INVENTION

This invention provides compounds of the formula:

$$\text{(I)}$$

or a pharmaceutically acceptable salt or solvate thereof, wherein:

(A) m is an integer selected from the group consisting of: 0, 1, and 2;

(B) n and p are integers and are each independently selected from the group consisting of: 0, 1, 2, and 3 such that the sum of n and p is 2 or 3 such that when the sum of n and p is 2, T is a 4-membered ring and when the sum of n and p is 3, T is a 5-membered ring;

(C) each $R^1$, $R^2$, $R^3$, $R^4$, $R^6$, $R^7$, and $R^8$ is independently selected from the group consisting of:

(1) H;

(2) $C_1$ to $C_6$ alkyl;

(3) $C_3$ to $C_6$ cycloalkyl; and (4) $-(CH_2)_q-R^9$ wherein q is an integer of: 1 to 7, and $R^9$ is selected from the group consisting of: phenyl, substituted phenyl, $-OR^{10}$, $-C(O)OR^{10}$, $-C(O)R^{10}$, $-OC(O)R^{10}$, $-C(O)NR^{10}R^{11}$, CN and $-SR^{10}$ wherein $R^{10}$ and $R^{11}$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents; examples of —$(CH_2)_1$—$R^9$ include benzyl, substituted benzyl and the like, wherein the substituents on the substituted benzyl are as defined above for said substituted phenyl;

(D) $R^5$ is selected from the group consisting of:
(1) H;
(2) $C_1$ to $C_{20}$ alkyl;
(3) $C_3$ to $C_6$ cycloalkyl;
(4) —C(O)O$R^{10'}$; wherein $R^{10'}$ is the same as $R^{10}$ defined below except that $R^{10'}$ is not H;
(5) —C(O)$R^{10}$;
(6) —C(O)N$R^{10}R^{11}$;
(7) allyl;
(8) propargyl; and
(9) —$(CH_2)_q$—$R^9$, wherein q and $R^9$ are as defined above with the proviso that when q is 1 when $R^9$ is not —OH or —SH;

(E) $R^{10}$ and $R^{11}$ are each independently selected from the group consisting of: H, $C_1$ to $C_6$ alkyl, and $C_3$ to $C_6$ cycloalkyl; and, for the substituent —C(O)N$R^{10}R^{11}$, $R^{10}$ and $R^{11}$, together with the nitrogen to which they are bound, can form a ring having 5, 6, or 7 atoms;

(F) the dotted line ( . . . ) represents a double bond that is optionally present when m is 1, and T is a 5-membered ring, and n is not 0, and p is not 0(i.e., the nitrogen in the ring is not bound directly to the carbon atom bearing the double bond), and when said double bond is present then $R^2$ and $R^8$ are absent;

(G) when m is 2, each $R^1$ is the same or different substituent for each m, and each $R^2$ is the same or different substituent for each m;

(H) when n is 2 or 3, each $R^3$ is the same or different substituent for each n, and each $R^4$ is the same or different substituent for each n, and (I) when p is 2 or 3, each $R^6$ is the same or different substituent for each p, and each $R^7$ is the same or different substituent for each p.

This invention also provides pharmaceutical compositions comprising a pharmaceutically acceptable carrier and an effective amount of a Compound of Formula I.

This invention further provides a method of treating allergy, (for example asthma), inflammation, hypertension, raised intraocular pressure (such as glaucoma)—i.e., a method of lowering intraocular pressure, sleeping disorders (e.g., hypersomnia, somnolence, narcolepsy and sleeplessness, such as insomnia), states of hyper and hypo motility and acidic secretion of the gastrointestinal tract, hypo and hyperactivity of the central nervous system (for example, agitation and depression) and other CNS disorders (such as Alzheimers, Schizophrenia, and migraine) comprising administering an effective amount of a compound of Formula I to a patient in need of such treatment.

DETAILED DESCRIPTION OF THE INVENTION

As used herein the following terms have the following meanings unless indicated otherwise:

alkyl—represents a straight or branched, saturated hydrocarbon chain having from 1 to 20 carbon atoms;

cycloalkyl—represents a saturated carbocyclic ring having from 3 to 6 carbon atoms; and halogen (halo)—represents fluoro, chloro, bromo or iodo.

Preferably, for compounds of Formula I, m is 0 or 1; $R^5$ is selected from the group consisting of H and $C_1$ to $C_{20}$ alkyl; and $R^1$ to $R^4$ and $R^6$ to $R^8$ are each independently selected from the group consisting of: H, $C_1$ to $C_6$ alkyl, and —$(CH_2)_q$—$R^9$ wherein $R^9$ is phenyl. Most preferably, $R^5$ is selected from the group consisting of H and methyl; and $R^1$, $R^2$, $R^3$, $R^4$, $R^5$, $R^6$, $R^7$, and $R^8$ are each independently selected from the group consisting of: H, methyl, ethyl, pentyl, benzyl, and 2-phenylethyl.

Representative compounds of this invention include compounds of the formula:

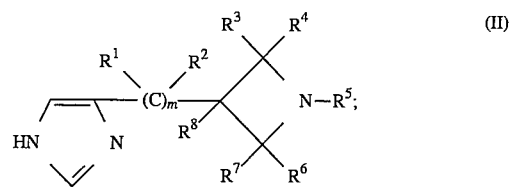

(II)

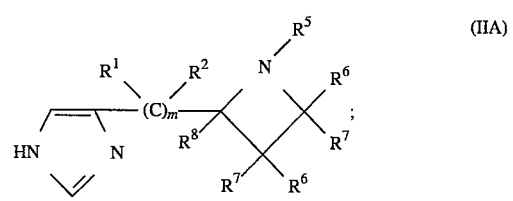

(IIA)

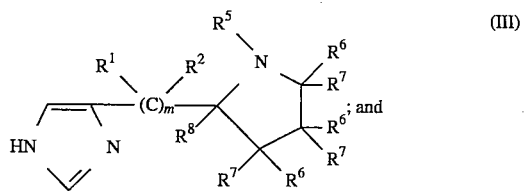

(III)

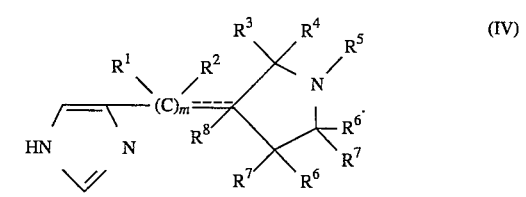

(IV)

wherein m and $R^1$ to $R^8$ are as defined for Formula I.

Representative compounds of Formula II include compounds of Formulas II-1, II-2 and II-3;

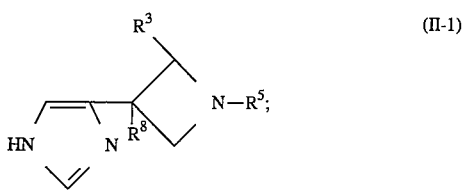

(II-1)

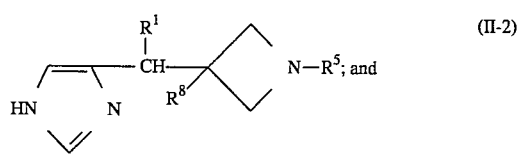

(II-2)

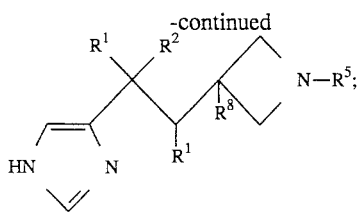
(II-3)

wherein $R^1$, $R^2$, $R^3$, $R^5$, and $R^8$ are as defined for Formula I.

Preferably, for compounds of Formula II, $R^3$, $R^4$, $R^6$, and $R^8$ are H. Preferred compounds of Formula II are represented by compounds of Formulas IIb and IIC:

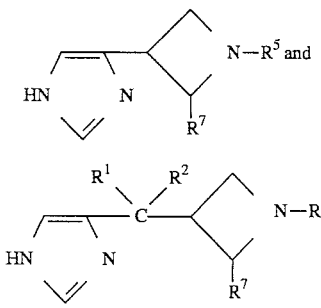
(IIB)

(IIC)

wherein $R^1$ and $R^2$ are as defined for Formula I with H being preferred, $R^5$ is as defined for Formula I with H and methyl being preferred and $R^7$ is selected from the group consisting of H, $C_1$ to $C_6$ alkyl, and $-(CH_2)_q-R^9$ wherein $R^9$ is phenyl. Preferably, $R^7$ is $C_1$ to $C_6$ alkyl, and most preferably methyl.

Representative compounds of Formula IIA include compounds of Formulas IIA-1 and IIA-2:

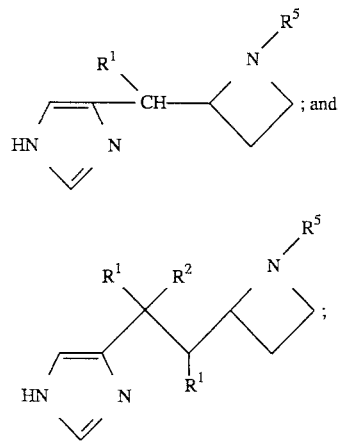
(IIA-1)

(IIA-2)

wherein $R^1$, $R^2$, and $R^5$ are as defined for Formula I.

Representative compounds of Formula III include compounds of Formulas III-1 and III-2:

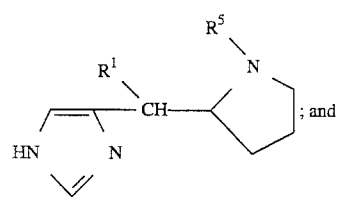
(III-1)

(III-2)

wherein $R^1$, $R^2$, and $R^5$ are as defined for Formula I.

Representative compounds of Formulas IV include compounds of Formulas IV-1, IV-2, IV-3, IV-4, IV-5, IV-6 and IV-7:

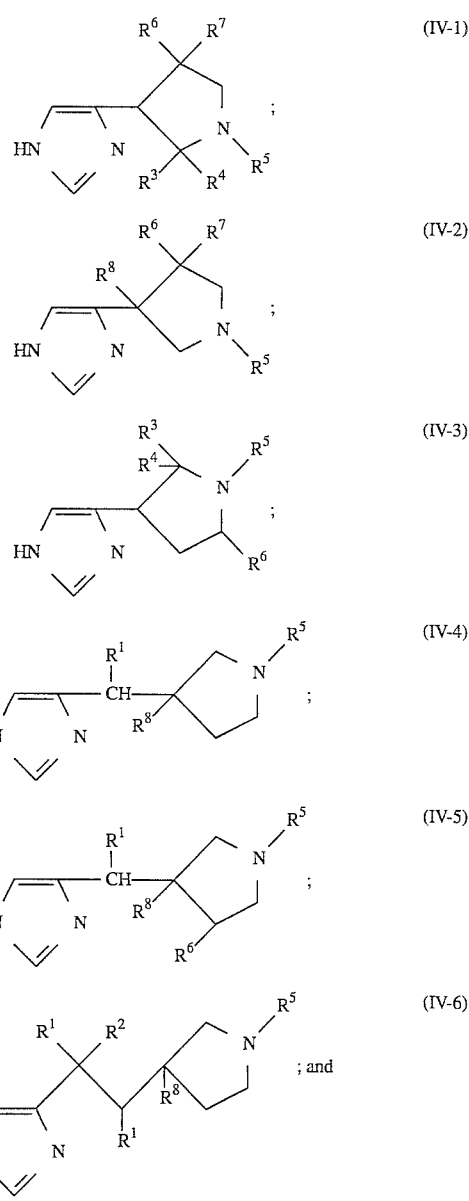
(IV-1)

(IV-2)

(IV-3)

(IV-4)

(IV-5)

(IV-6)

-continued
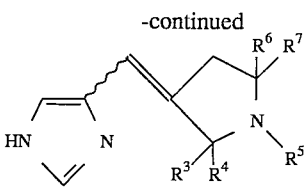
(IV-7)
wherein $R^1$, $R^2$, $R^3$, $R^4$, $R^5$, $R^6$, $R^7$, and $R^8$ are as defined for Formula I.
Representative compounds of Formula IV also include compounds of Formulas IV-8, IV-9, and IV-10:
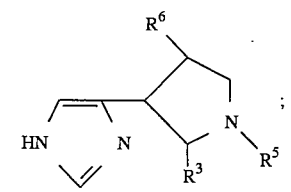
(IV-8)
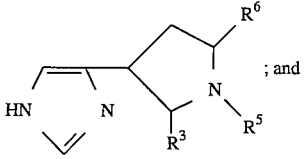
(IV-9)
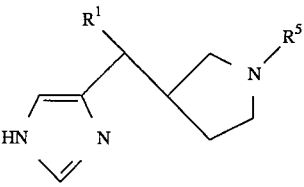
(IV-10)
wherein $R^1$, $R^3$, $R^5$, and $R^6$ are as defined for Formula I.
Representative compounds of Formulas I include:
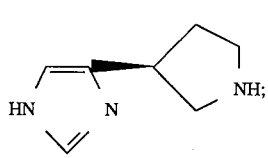
(A1)
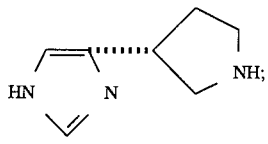
(A2)
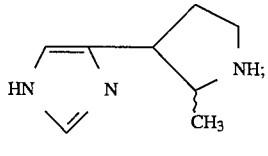
(B)
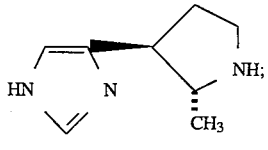
(B1)
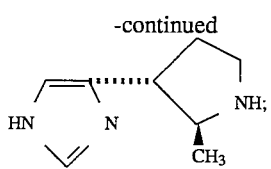
(B2)
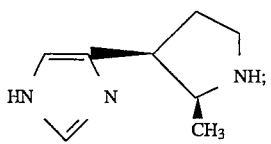
(B3)
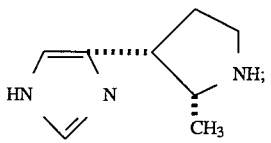
(B4)
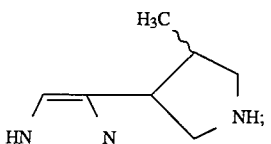
(C)
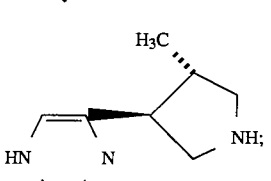
(C1)
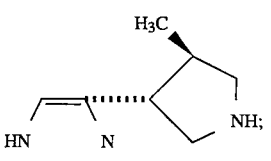
(C2)
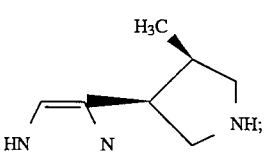
(C3)
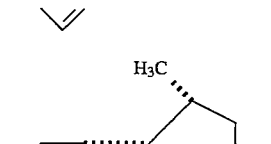
(C4)
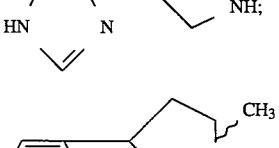
(D)

-continued
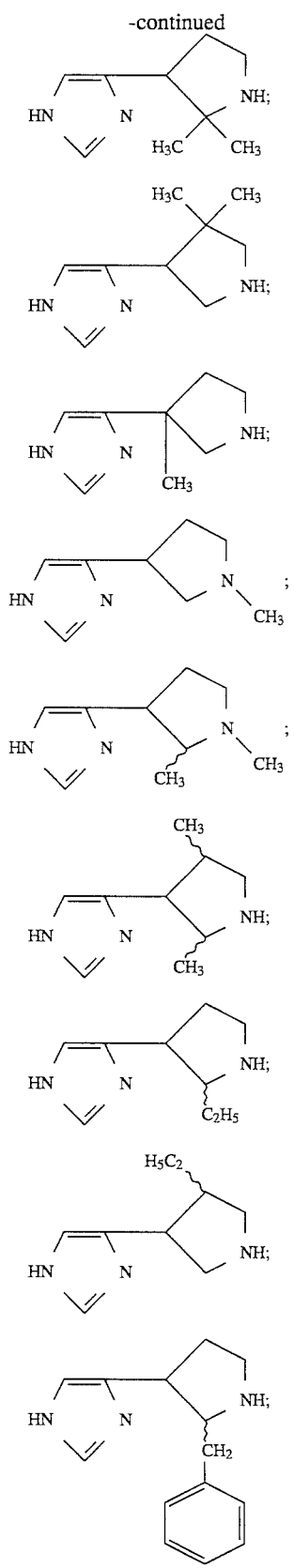
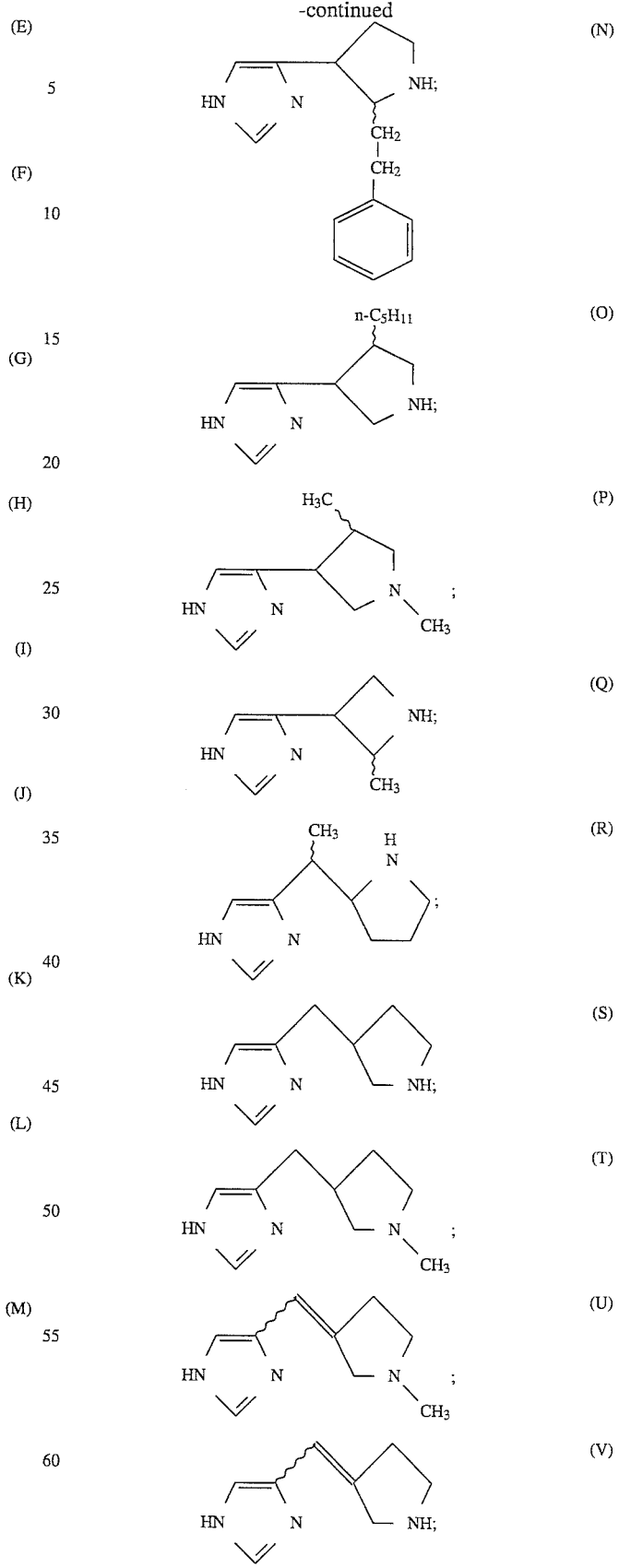

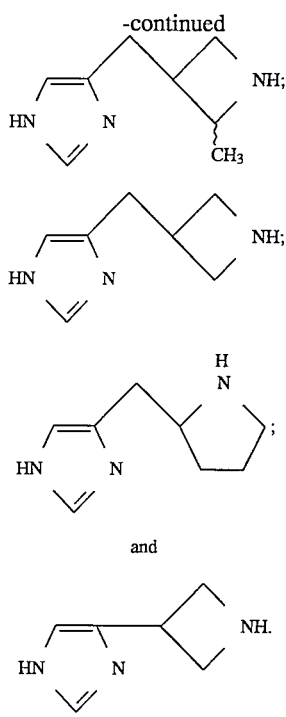

and

Certain compounds of the invention may exist in different isomeric (e.g., enantiomer and diastereoisomers) forms. The invention contemplates all such isomers both in pure form and in admixture, including racemic mixtures. Enol forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminium, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the nitrogen atoms may form salts with acids. Examples of suitable acids for salt formation are hydrochloric, sulfuric, phosphoric acetic, citric, oxalic, malonic, salicyclic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The following processes may be employed to produce compounds of Formula I. Unless stated otherwise, reactions are conducted at an appropriate temperature which allows the reaction to proceed at a reasonable rate to completion. Also, unless indicated otherwise, the substituent groups referred to in the following processes are as defined above in Formula I.

A. Preparation of Compounds Wherein m is 0, n is 1 and p is 1 Producing Compounds of Formula II Step 1—Preparation A

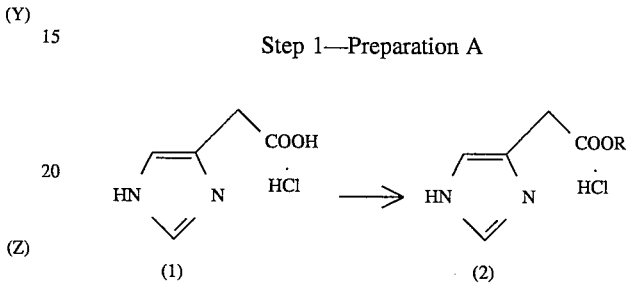

In step 1, commercially available compound (1* is dissolved in a suitable alcohol, ROH wherein R is a lower alkyl such as a $C_1$ to $C_6$ alkyl (e.g., methyl, ethyl, isopropyl and the like), preferably methanol, containing a catalytic amount of concentrated hydrochloric acid or similar acid. The reaction mixture is heated at a temperature of about 50° to about 70° C. to produce compound (2). There are many other esterification methods known in the art that may also be employed.

Step 2—Preparation A

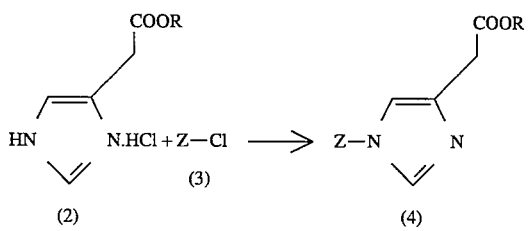

In Step 2, compound (2) is reacted with compound (3) in a polar organic solvent at a temperature of about 0° to about 50° C. in the presence of an organic base to produce compound (4). In compounds (3) and (4), Z represents the protecting group:

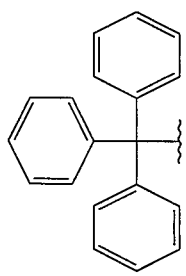

(trityl group). Z can be other protecting groups, such as 2-(trimethylsilyl)ethoxymethyl, benzyloxycarbonyl, and the like; however, unless stated otherwise, Z preferably represents the trityl group in the processes described below for making the compounds of this invention. Suitable organic solvents include: DMF (N,N-dimethylformamide), $CH_2Cl_2$ and the like. DMF is preferred. Preferably, triethylamine is used as the base. Other suitable bases include N,N-diisopropylethylamine and the like.

Those skilled in the art will appreciate that other protecting groups known in the art may be used—such as, for example, base sensitive groups wherein the protected compounds would be deprotected using basic conditions (e.g., NaOH). The processes described herein wherein the protected compound is deprotected under acidic conditions may also be carried out under basic conditions when a base sensitive protecting group is used.

Step 3—Preparation A

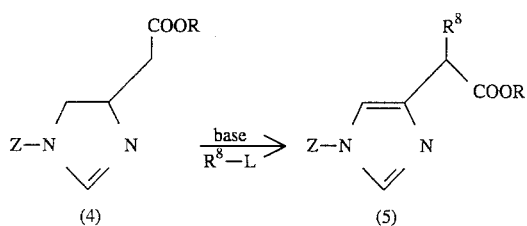

In Step 3, the enolate of compound (4) reacts with $R^8$—L in an organic solvent to produce compound (5). The reaction is conducted at a temperature in the range of about 0° to about 50° C. L is a suitable leaving group such as Cl, Br, I and the like. Preferably, LDA (lithium diisopropylamide) is used as the organic base to form the enolate, but other suitable bases include sodium hydride and the like. Suitable organic solvents include tetrahydrofuran, 1,4-dioxane and the like. Preferably, THF (tetyrahydrofuran) is used Step 4—Preparation A

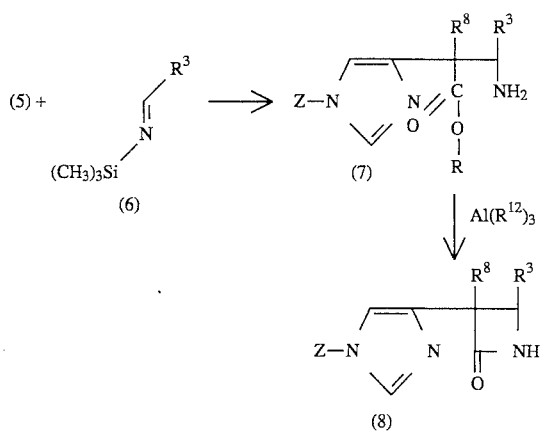

In Step 4, the enolate of compound (5) is reacted with compound (6) in an organic solvent in the presence of a Lewis acid to produce compound (7). Suitable organic solvents include tetrahydrofuran, diethyl ether, 1,4-dioxane and the like. Preferably, tetrahydrofuran or diethyl ether is used. Suitable organic bases used to generate the anion of (5) include lithium diisopropylamide, $LiN(Si(CH_3)_3)_2$, and NaH. Preferably, $LiN(Si(CH_3)_3)_2$ is used. Representative Lewis acids include $BF_3 \cdot (C_2H_5)_2O$, $(CH_3)_3SiCl$ and the like, with $BF_3 \cdot (C_2H_5)_2O$ being preferred. The reaction is conducted at a temperature within the range of about −78° to about 0° C.

Compound (7) is converted to compound (8) by reacting compound (7) with $Al(R^{12})_3$ in an organic solvent at a temperature of about 50° C. $R^{12}$ is a suitable alkyl group such as methyl, ethyl, isopropyl, butyl, and the like. Methylene chloride is a preferred solvent for this reaction, but others, such as 1,2-dichloroethane, can be employed.

Compound (6) in Step 4 is prepared according to known in the art procedures—for example: Cainelli et al., Tetrahedron Letters, Vol. 28, No. 44, p. 5369 (1987); and Uyehara et al., Tetrahedron Letters, Vol. 30, No. 32, p. 4275 (1989). In compound (6), $R^3$ is as defined above.

Steps 5, 6 and 7—Preparation A

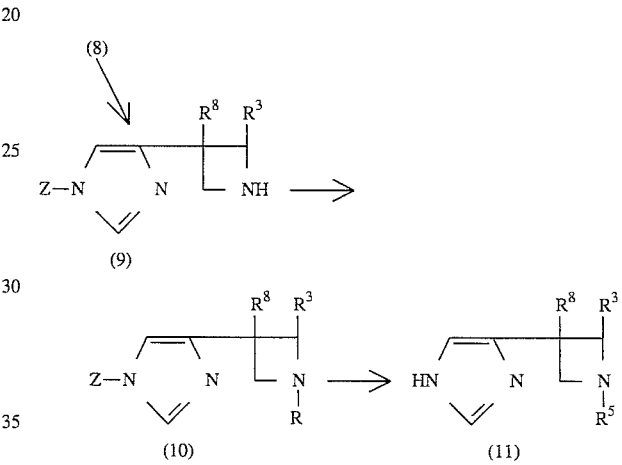

In Step 5, compound (8) is reduced to compound (9). The reaction is conducted in an organic solvent at a temperature within the range of about 20° to about 70° C. using a known reducing agent. Examples of suitable reducing agents include DIBALH (diisobutyl aluminium hydride) and $AlH_3$. Preferably tetrahydrofuran is used as the organic solvent, but other suitable solvents include 1,4-dioxane and the like.

In Step 6, compound (9) is reacted with (i) $R^5$—X (when $R^5$ is —$C(O)R^{10}$, —$C(O)OR^{10'}$, —$C(O)NR^{10}R^{11}$ or alkyl) in an organic solvent optionally in the presence of a suitable base (e.g., triethylamine) or (ii) $R^{5A}$—CHO (when $R^5$ is alkyl, cycloalkyl, allyl, propargyl, benzyl or substituted benzyl) in the presence of $NaBH_3(CN)$ (sodium cyanoborohydride) or other hydrogenating conditions (e.g. $H_2$/Rd/ROH) in an organic solvent; to produce compound (10). $R^{5A}$ represents an $R^5$ group that has one less —$CH_2$— group. Preferably, $CH_2Cl_2$ is used as the solvent when $R^5$—X is used, and tetrahydrofuran or an alcohol is used as the solvent when $R^{5A}$—CHO is used. X represents a suitable leaving group such as Cl, Br, I, or —$OCH_3$. The reaction ((i) or (ii)) can be performed at a temperature within the range of about −30 to about 80° C. Compound (10), when $R^5$ is —$C(O)NR^{10}H$, is prepared by reacting compound (9) with O=C=N—$R^{10}$ in an organic solvent, such as $CH_3CH$ or toluene. The reaction is performed at a temperature in the range of about 20° to about 110° C. Alternatively, compounds wherein $R^5$ is —$C(O)NR^{10}R^{11}$ may be made from compounds wherein $R^5$ is —$C(O)OR^{10'}$ by reacting such compounds with $NHR^{10}R^{11}$ in an organic solvent (e.g., THF) at a temperature of about 25° to about 100° C. Compound (9), or compound (10) wherein $R^5$ is —C(O)O(t-butyl), can be reacted with aqueous acid (e.g., HCl, HBr, and the like), at a temperature of about 25° to about 100° C., to produce compound (11) wherein $R^5$ is H.

In Step 7, compound (10) is deprotected by treatment with dilute aqueous acid, such as HCl or HBr, at a temperature of about 25° to about 90° C. to produce compound (11). Other protecting groups are removed by methods well known in the art.

In all the preparations that follow, intermediate compounds wherein the imidazole nitrogen is protected by Z and the nitrogen of the cyclic four or five membered amine is substituted with —C(O)O(t-butyl) or unsubstituted, i.e., hydrogen is bound to the amine nitrogen, such as in compounds (10) or (9), respectively, such intermediate compounds can be reacted with aqueous acid (e.g., HCl, HBr, and the like), at a temperature of about 25° to about 100° C., to produce deprotected final products wherein $R^5$ is H, e.g., the compound (11).

B. Preparation of Compounds Wherein m is 0, n is 1 and p is 2 Producing Compounds of Formula IV Step 1—Preparation B

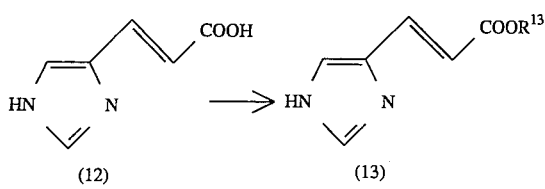

In Step 1, uracanic acid (12) is heated with catalytic amount of concentrated sulfuric acid in a solvent $R^{13}OH$ to produce a compound (13). $R^{13}$ is an alkyl group such as methyl, ethyl, and the like. The reaction is conducted at a temperature equivalent to the boiling point of the solvent ($R^{13}OH$), for example 65° C. for methanol.

Step 2—Preparation B

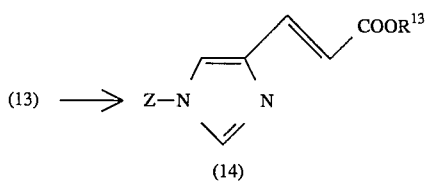

In Step 2, compound (13) is reacted with trityl chloride (see compound (3) in Preparation A above) to produce compound (14), wherein Z represents the tityl group. Other suitable compounds which provide protecting groups (Z) which can be used instead of trityl chloride include SEM (2-(trimethylsilyl)ethoxymethyl) chloride.

Step 3—Preparation B

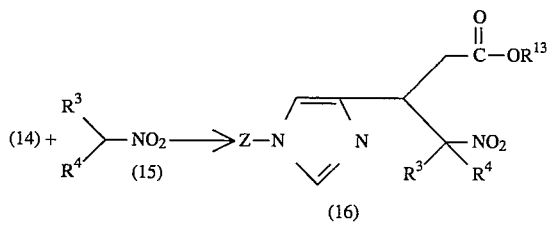

In Step 3, compound (14) (from Step 2) is reacted with compound (15) to produce compound (16). The reaction takes place at a temperature within the range of about 20° to about 100° C. in an organic solvent containing an organic base. Suitable organic bases include DBU (1,8diazabicyclo [5.4.0]undec-7-ene), and TMG (1,1,3,3-tetramethylguanidine). Suitable solvents include acetonitrile, tetrahydrofuran, N,N-dimethylformamide and the like.

Step 4—Preparation B

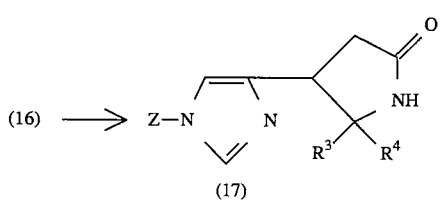

In Step 4, compound (16A) (from Step 3) is hydrogenated to produce compound (17). The hydrogenation takes place in an organic solvent, using Raney-Nickel, at a temperature of about 20° to about 60° C. Preferably ethanol is used as the organic solvent. Under these conditions cyclization occurs in situ to provide the desired lactam (17).

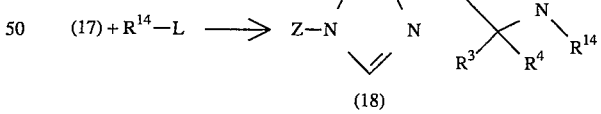

In Step 5, the anion of compound (17) is reacted with $R^{14}$—L to place the $R^{14}$ on the indicated nitrogen atom in compound (18). $R^{14}$ can be a suitable protecting group such as $Si(CH_3)_2C(CH_3)_3$ or —C(O)O(t-butyl), or $R^{14}$ can be an alkyl, cycloalkyl, benzyl, substituted benzyl, allyl, or propargyl group. L is a leaving group, such as Cl, Br, I or —OSO$_2$CF$_3$. The reaction is conducted in an organic solvent such as THF, diethyl ether, 1,4-dioxane or DMSO in the presence of a suitable base, such as lithium diisopropylamide or NaH. The reaction takes place at a temperature within the range of about −78° to about 80° C.

Step 6—Preparation B

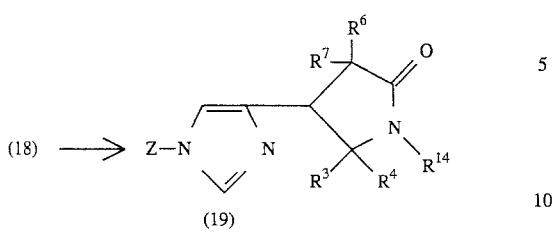

In Step 6, the enolate of compound (18) reacts with $R^6$—X and then with $R^7$—X to produce compound (19). X represents a suitable leaving group, such as Cl, Br, I or —$OSO_2CF_3$. Each reaction to place each substituent group on the ring takes place in an organic solvent using an organic base. Tetrahydrofuran is the solvent usually used; however, other suitable solvents include 1,4-dioxane, diethyl ether and the like. Examples of organic bases include lithium diisopropylamide, $M^+N[Si(CH_3)_3]_2$, KH and the like. $M^+$ represents a suitable metal cation such as Na, Li, K, and the like. The reaction is usually conducted at a temperature of about −78° to about 80° C.

Steps 7, 8 and 9—Preparation B

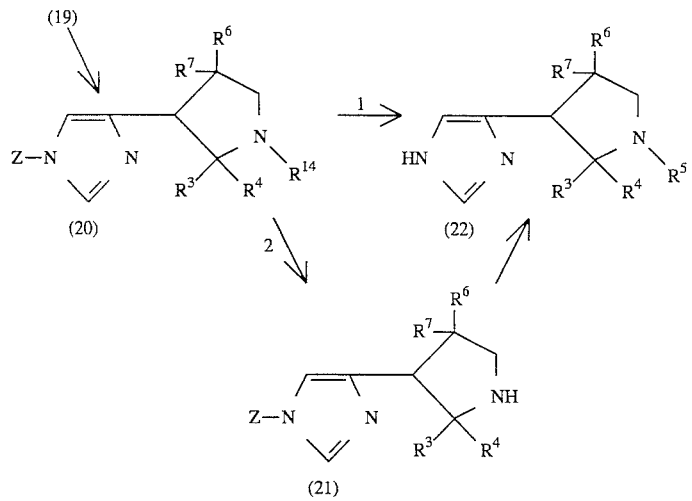

In Step 7, compound (19) is reduced to compound (20) with a reducing agent in an organic solvent at a suitable temperature. Preferably, $LiAlH_4$ (lithium aluminium hydride) is used with tetrahydrofuran at a temperature of about 0° to about 70° C. Other suitable reducing agents include $BH_3$ (borane) and the like. Other organic solvents which may be used include 1,4-dioxane and the like.

In reaction path 1 (compound (20) to (22)), $R^{14}$ is alkyl, cycloalkyl, benzyl, substituted benzyl, allyl, or propargyl. In reaction path 2 (compound (20) to (21)), $R^{14}$ is —$Si(CH_3)_2C(CH_3)_3$ or —C(O)O(t-butyl).

In Step 8, following reaction path 1, compound (20) is deprotected by following the procedure in Step 7 of Preparation A to produce compound (22). Alternatively, following reaction path 2, when $R^{14}$ is —$Si(CH_3)_2C(CH_3)_3$, compound (20) is treated with tetrabutylammonium fluoride in tetrahydrofuran at a temperature of about 0° to about 50° C. to produce compound (21), or compound (20), when $R^{14}$ is —C(O)O(t-butyl), is treated with dilute aqueous acid (e.g., HCl, HBr and the like).

In Step 9, the procedures in Steps 6 and 7 of Preparation A are followed so that compound (21) may be converted to compound (22).

C. Preparation of Compounds Wherein m is 0, n is 1 and p is 2 Producing Compounds of Formula IV

Step 1—Preparation C

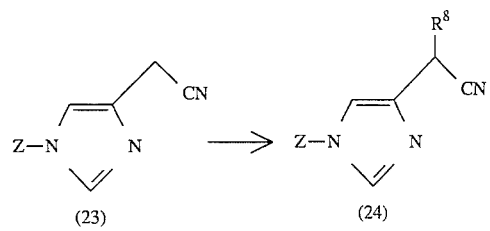

In Step 1, compound (23), synthesized according to Degraw et al. J. Med., 1977, 20, 1671, wherein Z id the trityl group, is reacted with $R^8$—L in an organic solvent, in the presence of an organic base, at a temperature of about 0° to about 50° C. to produce compound (24). L is a suitable leaving group such as, for example, halogen (halides) selected from the group consisting of: Cl, Br, and I; —$OSO_2$—$C_6H_4$—$CH_3$ (wherein $C_6H_4$ is phenyl); —$OSO_2$—$CH_3$; and the like. Suitable organic bases include lithium diisopropylamide, $LiN[Si(CH_3)_3]_2$, and the like. Preferably, the organic solvent is tetrahydrofuran. Other suitable solvents which may be used include 1,4-dioxane and the like.

Step 2—Preparation C

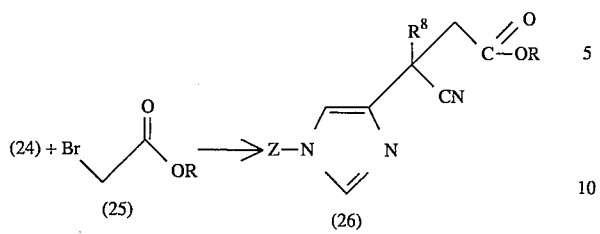

In Step 2, the anion of compound (24) is treated with compound (25) (wherein R is alkyl) to produce compound (26). The reaction is conducted at a temperature of about −78° to about 50° C. in an organic solvent containing an organic base. Suitable organic bases include lithium diisopropylamide, $LiN(Si(CH_3)_3)_2$, ad the like. Preferably, the organic solvent is tetrahydrofuran. Other suitable solvents which may be used include DMF and the like.

Steps 3 and 4—Preparation C

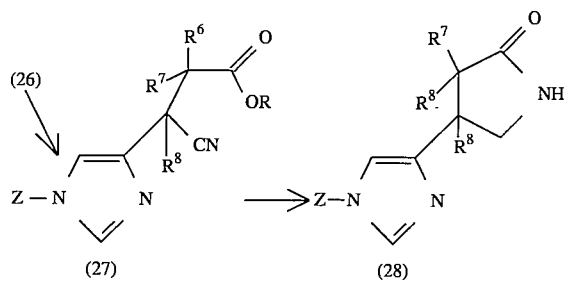

In Step 3, following the procedure set forth in Step 6 of Preparation B, compound (26) is substituted with substituted groups $R^6$ and $R^7$ to produce compound (27). Alternatively, compound (27) is prepared by the reaction of compound (24) with compound (26A)

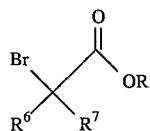

(26A)

under similar conditions for the reaction of compound (24) with compound (25).

In Step 4, compound (27) is reduced using $H_2$ and Raney-Nickel. The reduction takes place in ethanol at a temperature of about 25° (room temperature) to about 80° C. Other reducing agents can be used such as $NaBH_4/CoCl_2$ wherein the reduction takes place in ethanol at about room temperature. Subsequent cyclization in situ provides compound (28).

Steps 5,6 and 7—preparation C

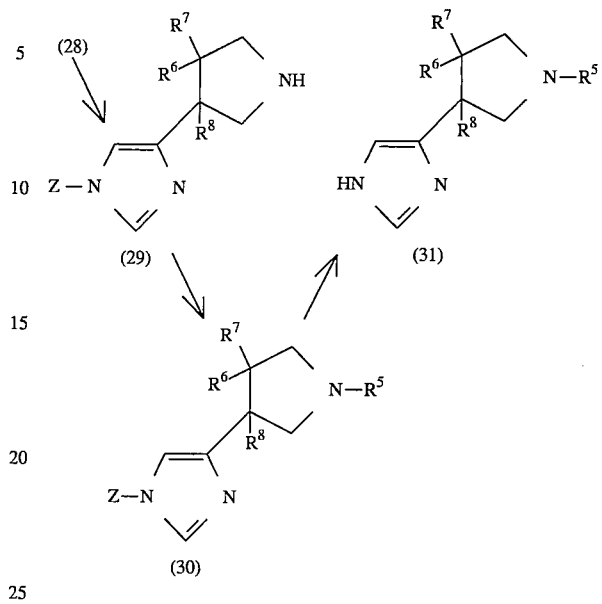

In Step 5, compound (28) is reduced to compound (29) in tetrahydrofuran using $LiAlH_4$ and a reaction temperature of about 0° to about 70° C. Another suitable reducing agent is $BH_3$.

In Step 6, compound (29) is converted to compound (30) according to the procedure described in Step 6 of Preparation A.

In Step 7, compound (30) is deprotected to produce compound (31) by following the procedure described in Step 7 of Preparation A.

D. Preparation of Compounds Wherein m is 0, n is 1 and p is 2 Producing Compounds of Formula IV

Step 1—Preparation D

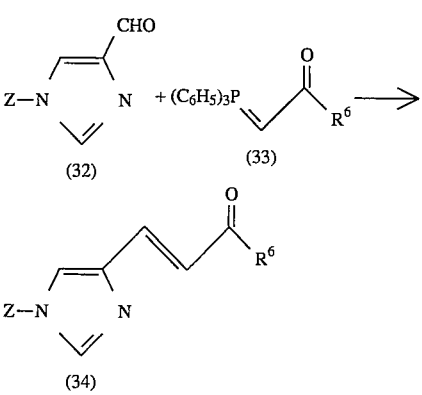

In Step 1, compound (32) is reacted with compound (33) to produce compound (34). The reaction is conducted in tetrahydrofuran at a temperature of about 25° to about 70° C. Other usable organic solvents besides tetrahydrofuran include DMF and the like. Compound (32) is prepared following the literature procedure set forth in J. L. Kelley et al., J. Med. Chem., 20, 721(1977). The Wittig reagent, compound (33) is either commercially available or may be prepared from the corresponding α-halo ketone and triphenylphosphine using standard reaction conditions known in the art.

Step 2—Preparation D

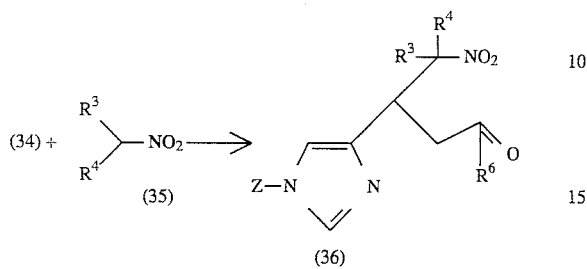

In Step 2, compound (34) is reacted with compound (35) to produce compound (36). The reactor is carried out according to the procedure set forth in Step 3 of Preparation B.

Steps 3, 4 and 5—Preparation D

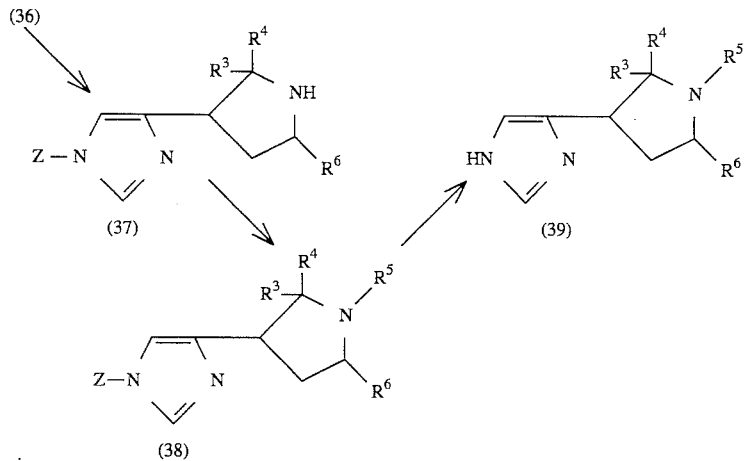

In Step 3, compound (36) is hydrogenated at a temperature of about 25° to about 70° C. using $H_2$ and Raney-Nickel. The reaction is conducted in ethanol in similar fashion to the reaction described in Step 4 of Preparation C.

In Step 4, following the procedure in Step 6 of Preparation A, compound (37) is reacted with $R^5$—X or $R^{5A}$—CHO to produce compound (38).

In Step 5, compound (38) is deprotected at a temperature of about 50° to about 100° C. using aqueous acid such as 10% aqueous hydrochloric acid to produce compound (39).

E. Preparation of Compounds Wherein m is 1, n is 0 and p is 2 or 3 Producing Compounds of Formulas IIa and III Step 1—Preparation E

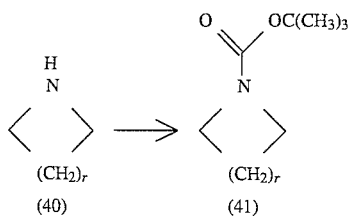

In Step 1, compound (40) is reacted with di-tert-butyl dicarbonate ($(tBOC)_2O$) in an organic solvent in the presence of an organic base. The reaction is conducted at a temperature of about 0° to about 30° C. Preferably, methylene chloride is used as the organic solvent, but other suitable organic solvents include DMF and the like. Triethylamine is used as the organic base. Other bases which can be used include 3-dimethylaminopyridine and the like. In compounds (40) and (41) r represents 1 or 2. The desired starting reactant (40) can be obtained commercially. In compound (41), the BOC group is chosen as an activating group or nitrogen which increases the kinetic acidity of the α-proton such that a lithio salt would result (for example, Step 2). Other activating groups or nitrogen, known in the art that can also be employed include nitroso, phosphoryl, hindered acyl, and formamidyl. (see Alrichimica Acta, Vol. 8, No. 3, 1985).

Step 2—Preparation E

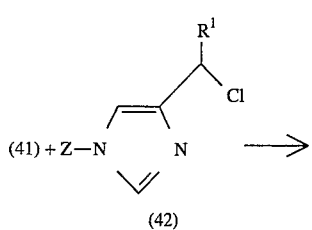

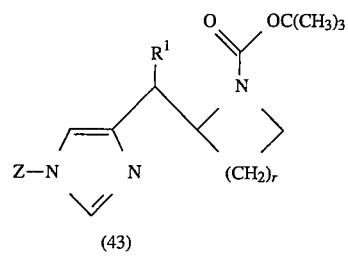

In Step 2, the anion of compound (41) is reacted with compound (42), to produce compound (43). The reaction is conducted in an organic solvent containing an organic base and TMEDA (tetramethylethylenediamine). The reaction is conducted at a temperature of about −78° to about 25° C. (room temperature). Tetrahydrofuran is preferably used as the solvent, other suitable solvents include diethyl ether and the like. The anion of (41) is prepared by metalation of (41) with sec-butyllithium in THF at −78° C. Compound (42) is obtained by reacting compound (32) with an organometallic reagent $R^1M$, wherein M is Li or MgBr, and then with thionyl chloride ($SOCl_2$).

Steps 3 to 5—Preparation E

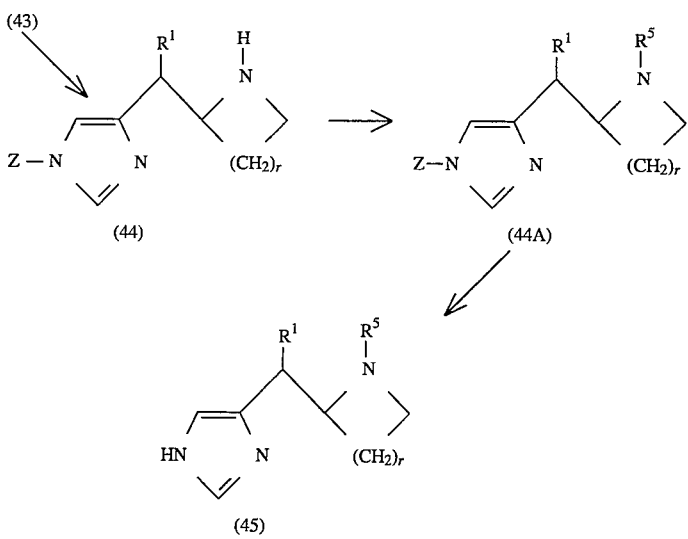

In Step 3, compound (43) is treated with HCl or similar acid in an inert organic solvent such as ethyl acetate or dioxane, at a temperature of about 0° C. to selectively deprotected (43) thus producing compound (44).

In Step 4, compound (44) is reacted with $R^5$—X or $R^{5A}$—CHO in accordance with the procedure set forth in Step 6 of Preparation A to produce compound (44A).

In Step 5, compound (44A) is then deprotected to produce compound (45) by following the procedure set forth in Step 7 of Preparation A.

F. Preparation of Compounds Wherein m is 1, n is 0 and p is 2 or 3 Producing Compounds of Formulas IIa and III

Step 1—Preparation F

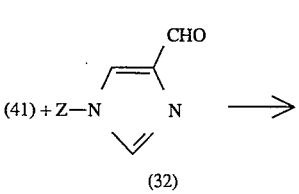

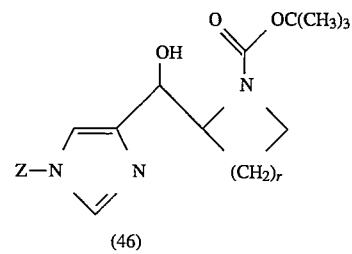

In Step 1, compound (41)—see Step 1 of Preparation E—is reacted with compound (32) in accordance with the procedure set forth in Step 2 of Preparation E. r is 1 or 2.

Steps 2 and 3—Preparation F

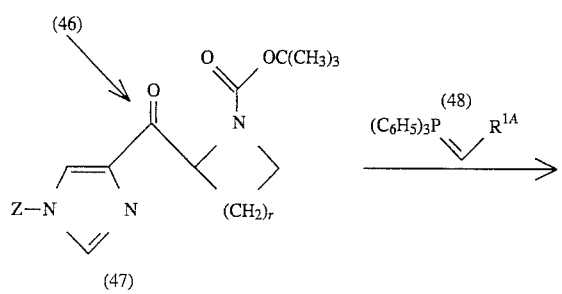

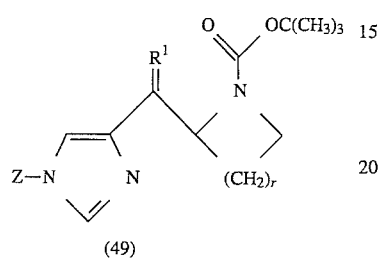

In Step 2, compound (46) is oxidized to produce compound (47). The oxidation is accomplished by treating compound (46) with an oxidizing agent, such as $MnO_2$ or PDC (pyridinium dichromate), in an inert organic solvent, such as tetrahydrofuran or methylene chloride, at a temperature of about 20° to about 70° C.

In Step 3, compound (47) reacts, under usual Wittig reaction conditions, with compound (48) in an organic solvent at a temperature of about 25° to about 70° C. to produce compound (49). In compound (48), $R^{1A}$ represents an $R^1$ group which has one less —$CH_2$— group. Preferably, the organic solvent is tetrahydrofuran; however, other suitable solvents, such as 1,4-dioxane and the like, can be used.

Steps 4 and 5—Preparation F

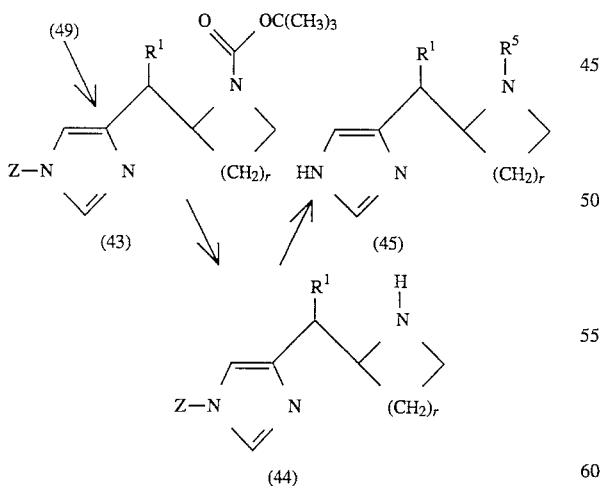

In Step 4, compound (43) is produced when compound (49) is hydrogenated in tetrahydrofuran with $H_2$ using a Pd—C (palladium/carbon) catalyst. Other organic solvents which can be used include ethyl acetate, methanol and the like. Other suitable metal catalysts such as Pt, Pd—$Al_2O_3$, Ra—Ni, NiB, and Pd—$CaCO_3$ can also be employed as the hydrogenation catalyst.

In Step 5, conversion of compound (43) to compound (44) and then to compound (45) is accomplished by following the same process described in Steps 3, 4, and 5 of Preparation E.

G. Preparation of Compounds Wherein m is 1, n is 1 and p is 1 or 2 Producing Compounds of Formulas II and IV Step 1—Preparation G

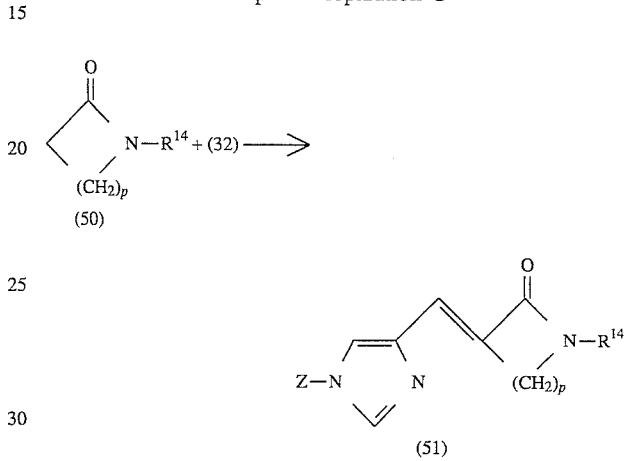

In Step 1, the anion of compound (50) reacts with compound (32) in an organic solvent at a temperature of about −78° to about 25° C. to produce compound (51) wherein p is 1 or 2. Suitable organic solvents include tetrahydrofuran and the like. Preferably, the organic base used to generate the anion of (50) is lithium diisopropylamide or $M^+N[Si(CH_3)_3]_2$ wherein $M^+$ is a metal cation such as Li, Na, or K. Z is trityl. Compound (50) is obtained from the commercially available unprotected precursor

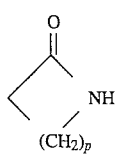

according to known methods—see, for example, Step 5 of Preparation B.

Steps 2–4—Preparation G

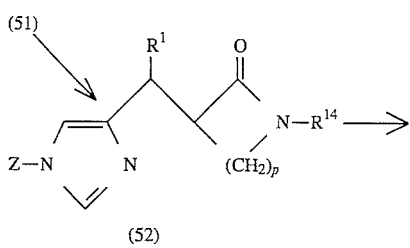

31

-continued

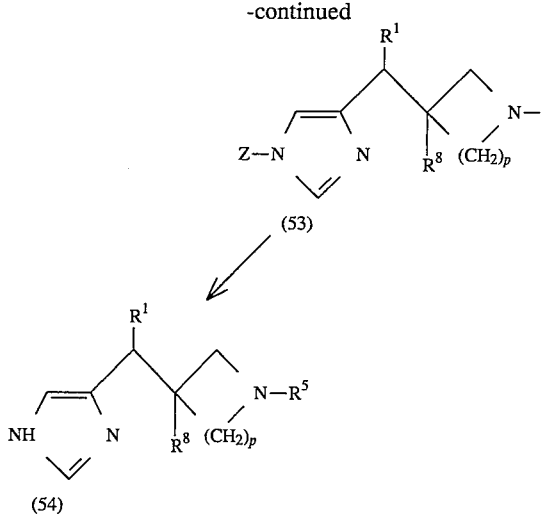

(53)

(54)

In Step 2, compound (51) is reacted with $R^1$—Q, wherein Q is Li or MgBr, in tetrahydrofuran containing CuCN and a Lewis acid, such as $BF_3$, $(CH_3)_3SiCl$ and the like, to produce compound (52). The reaction is conducted at a temperature of about −78° to about 20° C. Tetrahydrofuran is the preferred organic solvent; however, other suitable solvents include diethyl ether and the like.

In Step (3), compound (52) is reacted with $R^8$—L according to the procedure set forth in Step 3 of Preparation A. Then the resulting $R^8$ substituted compound is reduced with either $AlH_3$ or DIBALH (when p=1); or with $LiAlH_4$ (when p=2) at a temperature of about 25° to about 65° C. to produce compound (53). The reduction is conducted in tetrahydrofuran; however, other organic solvents, such as 1,4-dioxane and the like, can be used.

In Step 4, compound (53) is converted to compound (54) according to the processes described in Steps 8 and 9 of Preparation B for the conversion of compound (20) to compound (22).

H. Preparation of Compounds Wherein m is 1, n is 1 and p is 1 or 2 Producing Compounds of Formulas II and IV The anion of compound (50), which is prepared by reacting compound (50) with lithium diisopropylamide at a temperature of about −20° C. to about 20° C. in THF (see Step 1 of Preparation G) reacts with compound (42)—see Step 2 or Preparation E—in tetrahydorfuran at a temperature of about −78° to about 25° C. to produce compound (52)— see Step 2 Preparation G. Other suitable solvents besides tetrahydrofuran can also be used, such as DMF and the like. Other suitable bases which can be used to generate the anion of (50) include $NaN[Si(CH_3)_3]_2$, $KN[Si(CH_3)_3]_2$, KH and the like. Compound (52) is converted to compound (54) following the procedures in Steps 3 and 4 of Preparation G.

32

I. Preparation of Compounds Wherein m is 1, n is 1 and p is 2

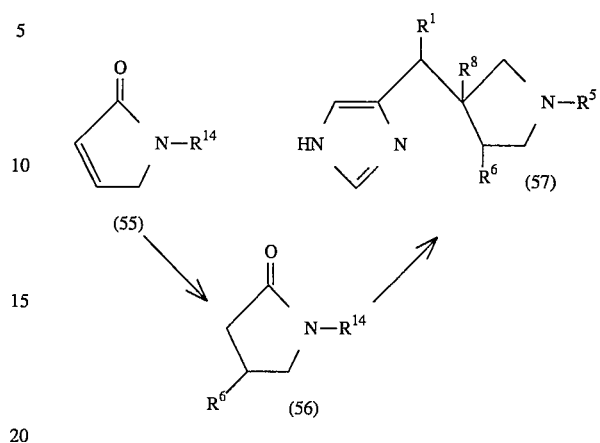

(55)

(56)

(57)

Compound (55) reacts with $R^5$—M (wherein M is Li, ZnBr or MgBr) in tetrahydrofuran containing $BF_3 \cdot (C_2H_5)_2O$ and CuCN at a temperature of about −78° to about 20° C. to produce compound (56). Other suitable solvents such as diethyl ether can be used. Compound (56) is converted to compound (57) in accordance with the reaction steps set forth in Preparation G or Preparation H.

Compound (55) is obtained by reacting the commercially available unprotected precursor

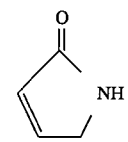

with $R^{14}$—L according to known methods—see, for example, Step 5 of Preparation B.

J. Preparation of Compounds Wherein m is 2, n is 0 and p is 2 or 3; or m is 2, n is 1 and p is 1 or 2

By following the steps in Preparation E, F, G, or H with the reception that compound (58)

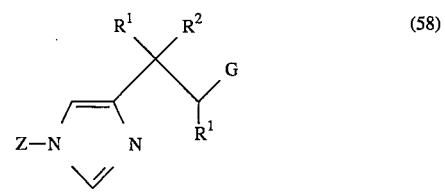

(58)

is used instead of compound (42) and compound (59)

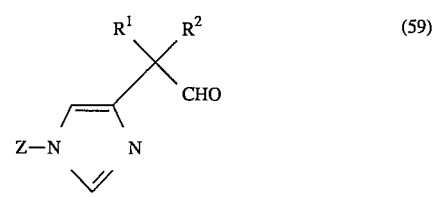

(59)

is used in place of compound (32), compounds (60) and/or (61)

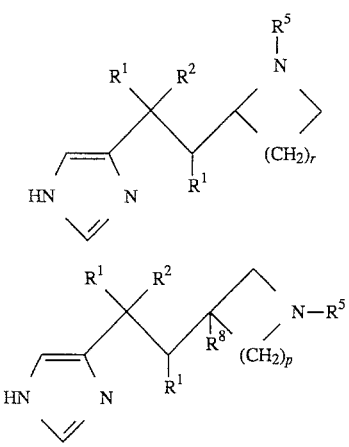

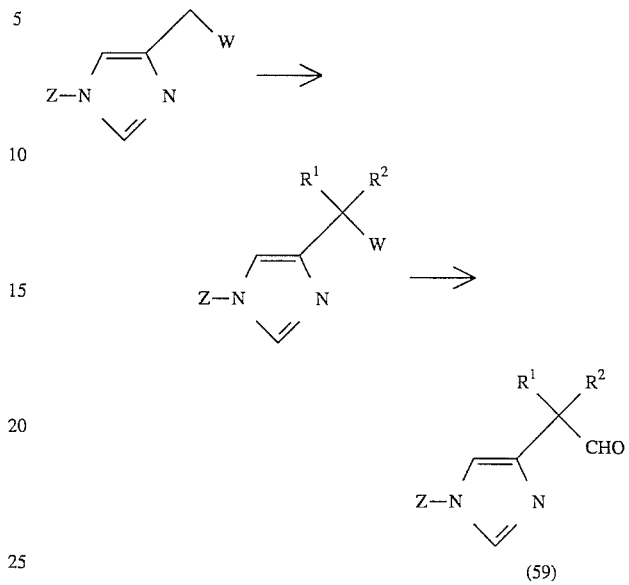

are produced. Compound (60) is produced following Preparation E or Preparation F, and compound (61) is produced following Preparation G or Preparation H. In compound (60), r is 1 or 2 and therefore p is 2 or 3, and in compound (61), p is 1 or 2. In compound (58), G represents a suitable leaving group such as Br, I, —OSO$_2$—C$_6$H$_4$—CH$_3$, —OSO$_2$—CH$_3$, —OSO$_2$—CF$_3$ and the like. The preparation of compound (58) is described below.

K. Preparation of Compound (58)

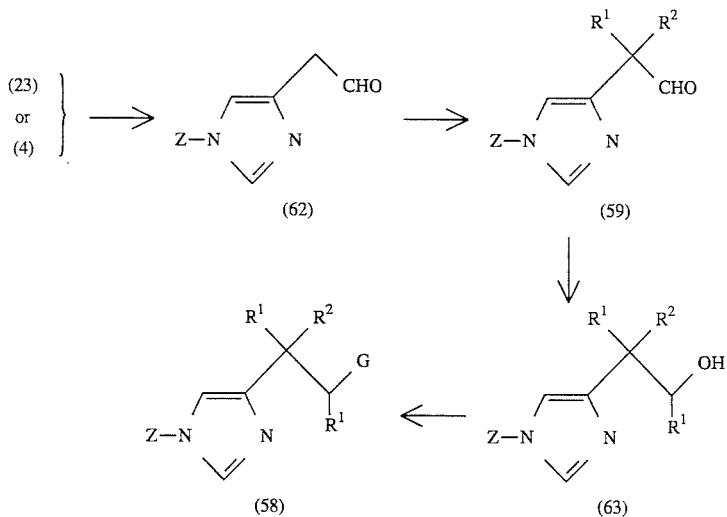

Compound (62) is produced by the reduction of compound (23) in tetrahydrofuran at a temperature of about 0° to about 70° C. using diisobutylaluminium hydride as the reducing agent followed by an aqueous work up. Alternatively, reduction of compound (4) by bis(2-methoxyethoxy)aluminium hydride also can produce compound (62), see for example R. Kanazawa & T. Tokoroyama, Synthesis, 526(1976). Compound (59) is produced by reacting compound (62) in an organic solvent containing an organic base with R$^1$—L and then with R$^2$—L in accordance with the method set forth in Step 3 of Preparation A. Preferably, the organic solvent is tetrahydrofuran and the organic base is lithium diisopropylamide. L is a suitable leaving group such as Cl, Br, I, —OSO$_2$—CF$_3$ and the like.

Alternatively, the sequence of the preparation of compound (59), from compound (4) or (23), can be switched, i.e., alkylation first to introduce R$^1$ and R$^2$ and then reduction.

-continued

W = COOR (4)
W = CN (23)

Compound (59) then reacts with either lithium aluminum hydride (when R$^1$=H) or R$^1$—Q (R$^1$ is not H) in tetrahydrofuran at a temperature of about −78° to about 0° C. to produce compound (63). Q represents Li or MgBr. When G represents a halide (i.e., Cl, Br, or I), then compound (58) is produced by either reacting compound (63) with (H$_5$C$_6$)$_3$P/CG$_4$ or (H$_5$C$_6$)$_3$PG$_2$ (see Fiser & Fiser, Reagents for Organic Synthesis, Vol. 1, p1247(1967)). When G represents —OSO$_2$—C$_6$H$_4$—CH$_3$, —OSO$_2$—CH$_3$ or —OSO$_2$—CF$_3$, then compound (58) is produced by reacting compound (63) with Cl—SO$_2$—C$_6$H$_4$—CH$_3$, Cl—SO$_2$—CH$_3$ or Cl—SO$_2$—CF$_3$, respectively, in methylene chloride containing triethylamine (as base) at a temperature of about –78° to about 0° C.

L. Preparation of Compounds Wherein m is 1, n is 1 and p is 2 and Wherein the Double Bond Indicated in Formula I is Present

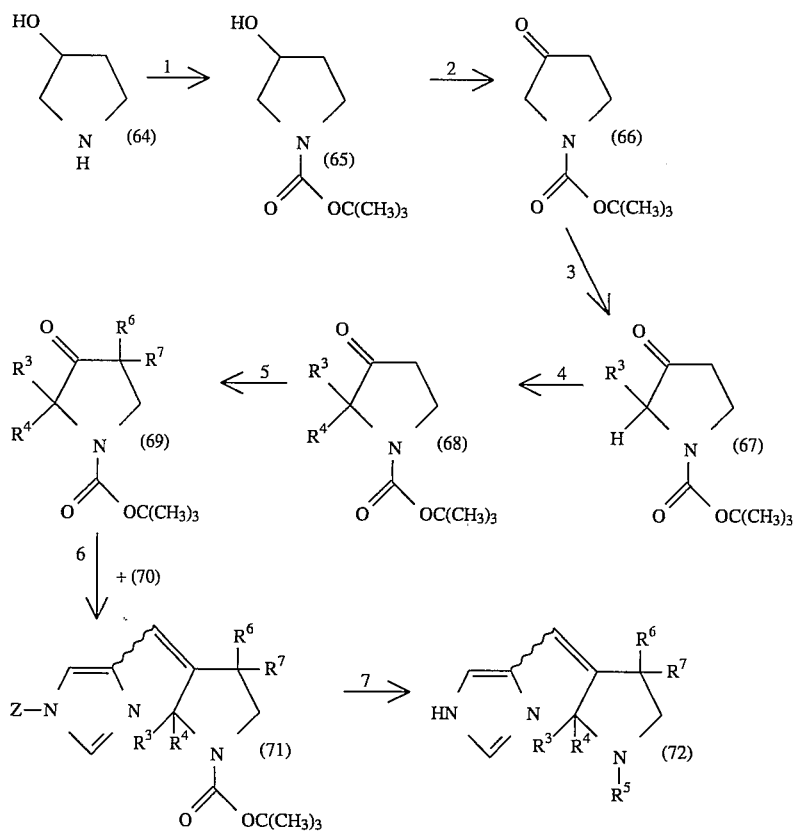

In Step 1, compound (65) is produced when compound (64) is reacted with (t—BOC)$_2$O and triethylamine. The reaction is conducted in an organic solvent, such as methylene chloride or DMF, using a temperature within the range of about 0° to about 25° C. (room temperature).

In Step 2, compound (66) is produced by treating compound (65) with an oxidizing agent such as pyridinium dichromate. The oxidation reaction is conducted in an organic solvent, such as methylene chloride, using a temperature of about 25° to about 50° C.

In Step 3, compound (67) is produced when the enolate of compound (66) is reacted with R$^3$—L wherein L is a suitable leaving group, such as halogen (e.g., Cl, Br, or I), —OSO$_2$CF$_3$ and the like. The reaction takes place in an organic solvent, such as tetrahydrofuran or benzene, containing a suitable base, such as NaH, LDA, or LiN(Si(CH$_3$)$_3$)$_2$. Preferably, tetrahydrofuran is used as the solvent and LDA is used as the base. The reaction is conducted at a temperature of about 0° to about 80° C.

In Step 4, compound (67) is reacted with R$^4$—L using the same procedure set forth in Step 3 in order to produce compound (68).

In Step 5, compound (69) is produced when compound (68) is first reacted with R$^6$—L and then reacted with R$^7$—L. Each reaction is conducted using the same procedure set forth in Step 3.

In Step 6, compound (71) is obtained when compound (69) is reacted with compound (70)

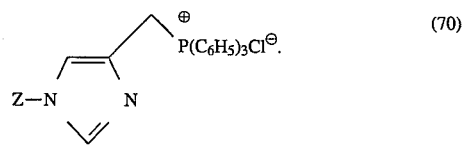

The reaction takes place in an organic solvent, such as tetrahydrofuran, DMF or benzene, containing a suitable base, such as NaH, LDA, or LiN(Si(CH$_3$)$_3$)$_2$. Preferably, tetrahydrofuran is used as the solvent and LDA is used as the base. The reaction is conducted at a temperature of about 0° to about 80° C. Compound (70) is obtained by reacting

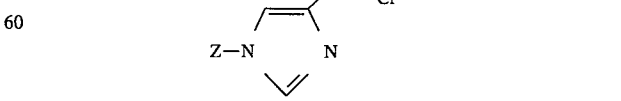

with P(C$_6$H$_5$)$_3$ in an organic solvent, such as methylene chloride, CH$_3$CN, tetrahydrofuran and the like, using a temperature of about 25° to about 50° C. In compounds (70) and (70A), Z represents trityl or SEM.

In Step 7, compound (72) is produced by using compound (71) and following the same procedures set forth in Steps 3, 4 and 5 of Preparation E.

In the steps of Preparation L, alkylations (i.e., Steps 3, 4 and 5) are only if desired and $R^3$, $R^4$, $R^5$, $R^6$, and $R^7$ are as defined for Formula I.

In the above processes, certain functional groups may be incompatable with some transformations described herein and consequently it is sometimes desirable and/or necessary to protect certain groups during the reactions. Certain protecting groups are employed in the above processes but, as those skilled in the art will recognize, other protecting groups may be used in their place. Conventional protecting groups are operable as described in Greene, T. W., and Wuts, P. G. M., "Protective Groups in Organic Synthesis," John Wiley & Sons, New York, 1991; the disclosure of which is incorporated herein by reference thereto. After the reaction or reactions, the protecting groups may be removed by standard procedures.

The compounds of this invention are either agonists or antagonists of the histamine $H_3$ receptor. The binding affinity of the compounds of the invention to the $H_3$ receptor may be demonstrated by the procedure described below:

$H_3$ Receptor Binding Assay

The source of the $H_3$ receptors in this experiment was guinea pig brain. The animals used weighted 400–600 g. The tissue was homogenized using a Polytron in a solution of 50 mM Tris, pH 7.5. The final concentration of tissue in the homogenization buffer was 10% w/v. The homogeneates were centrifuged at 1000×g for 10 min. in order to remove clumps of tissue and debris. The resulting supernatants were then centrifuged at 50,000×g for 20 min. in order to sediment the membranes, which were next washed 3 times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/mL with 0.1% DMSO. Membranes were then added (400 μg of protein) to the reaction tubes. The reaction was started by the addition of 3 nM [$^3$H]R-α-methylhistamine (8.8 CVmmol) or [$^3$H]-N-methylhistamine (80 Cvmmol) and incubated at 30° for 30 min. Bound ligand was separated from unbound ligand by filtration, and the amount of radioactive ligand bound to the membranes were performed in duplicate and the standard error was less than 10% in all instances. Compounds that inhibited greater than 70% of the specific binding of radioactive ligand to the receptor were serially diluted to determine a $K_i$ (μM). The results are given in Table 2.

In Table 2, the compound represented by (a*) is known in the art.

TABLE 2

| COMPOUND | $H_3$ Binding $K_i$ (μM) | COMPOUND | $H_3$ Binding $K_i$ (μM) |
| --- | --- | --- | --- |
| (a*) | 0.014 | (b) (±) | 0.007 |
| (c) (±) | 0.003 | (d) (±) | 0.006 |
| (e) | 0.17 | (f) (±) | 0.008 |

TABLE 2-continued

| COMPOUND | $H_3$ Binding $K_i$ (μM) | COMPOUND | $H_3$ Binding $K_i$ (μM) |
| --- | --- | --- | --- |
| (g) | 0.076 | (h) | 0.066 |
| (i) | 0.60 | (j) | 0.11 |
| (k) R' is methyl | 0.003 | (l) | 0.15 |
| (m) | 0.077 | (n) | 0.45 |
| (o) | 7%** | (p) | 68%** |

In Table 2, the "**" values for compounds (o) and (p) represent the % inhibition at a concentration of 2 μg/mL. It is expected that a higher concentrations higher activities will be obtained.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides of cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg to 500 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 1 mg to 2000 mg/day preferably 10 to 1000 mg/day, in one to four divided doses to achieve relief of the symptoms. The compounds are non-toxic when administered within this dosage range.

The invention disclosed herein is exemplified by the following preparative examples, which should not be construed to limit the scope of the disclosure. Alternative mechanistic pathways and analogous structures within the scope of the invention may be apparent to those skilled in the art.

EXAMPLE 1

A. Preparation of Methyl Ester (2)

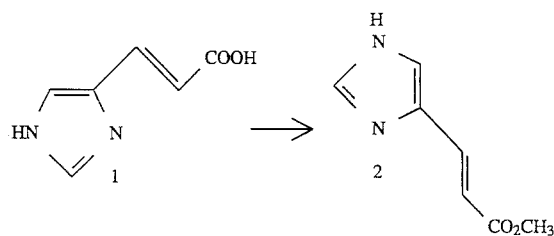

To a suspension of urocanic acid 1 (13.8 g, 100 mmol) in methanol (250 mL) was added concentrated sulfuric acid (10 mL) and the mixture was heated to reflux for 24 h. The mixture was cooled to 5° C. and concentrated ammonium hydroxide (25 mL) was added slowly. The solvents were removed by rotary evaporation and to the residue was added water (50 mL) and ethyl acetate (750 mL). The mixture was shaken, the layers separated, and the aqueous layer was extracted with ethyl acetate (500 mL). The combined organic layers were dried over anhydrous sodium sulfate, filtered and evaporated to give 2 as a white solid (14.9 g, 98%).

B. Preparation of (2-Trimethylsily)ethoxymethyl-imidazole (3)

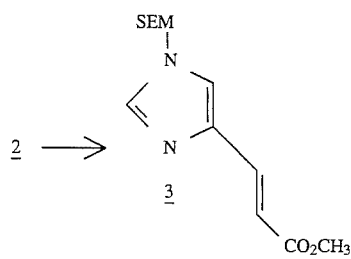

To a suspension of the methyl ester 2 (12.2 g, 80.0 mmol) in tetrahydrofuran (80 mL) was added triethylamine (28 mL, 200 mmol) and then (2-trimethylsilyl)ethoxymethyl chloride (30 mL, 170 mmol). The mixture was stirred at room temperature for 1 h and then to this mixture was added 5% aqueous sodium hydroxide (200 mL) and methylene chloride (1200 mL). The mixture was shaken vigorously, the layers separated, and the aqueous layer was extracted with methylene chloride (1200 mL). The combined organic layers were dried over anhydrous sodium sulfate, filtered, and evaporated to give an orange, oily residue which was purified by flash chromatography (ethyl acetate) to give 3 as a slightly yellow solid (10.8 g, 48%).

C. Preparation of Nitro-Ester (4)

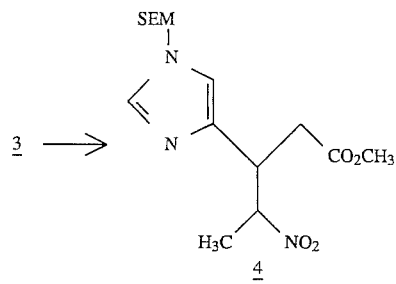

To a solution of unsaturated ester 3 (10.8 g, 38 mmol) in acetonitrile (25 mL) was added nitroethane (15 mL, 209 mmol) and then 1,8-diazabicyclo[5.4.0]undec-7-ene (6 mL, 40 mmol). The mixture was stirred at room temperature for 72 h, the solvents were removed by rotary evaporation and the dark, oily residue was purified by flash chromatography (ethyl acetate) to give the nitro-ester 4 as a mixture of diastereomers (13.3 g, 97%).

D. Preparation of Lactams (5t) and (5c)

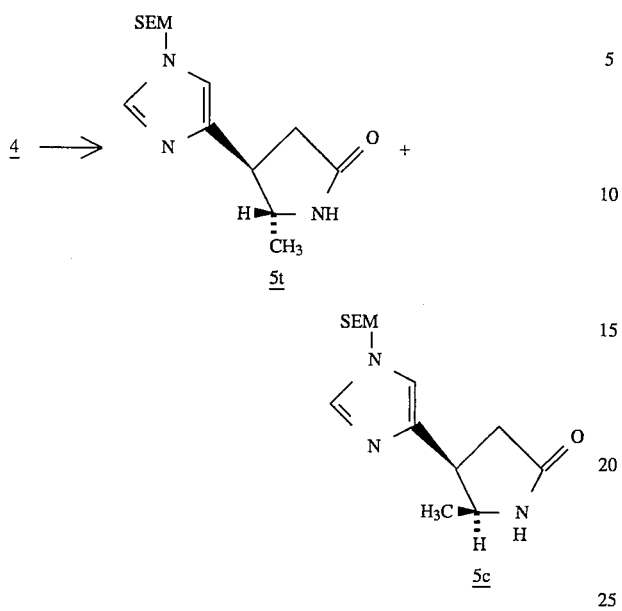

A mixture of the nitro-ester 4 (8.3 g, 23 mmol) and Raney nickel (8 g) in absolute ethanol (60 mL) was shaken under 60 psi of hydrogen at 55° C. in a Parr apparatus for 6 h. The mixture was filtered and the filtrate was evaporated to give an oily residue which was purified by flash chromatography (a: 5% MeOH/NH$_3$ in CH$_2$Cl$_2$, b: 7% MeOH/NH$_3$ in THF-:Hexane, 2:1) to give two compounds; the first compound to elute was the trans-diastereomer 5t (2.64 g, 39%). The second compound to elute was the cis-diastereomer 5c (1.67 g, 26%).

E. Preparation of pyrrolidine (6t)

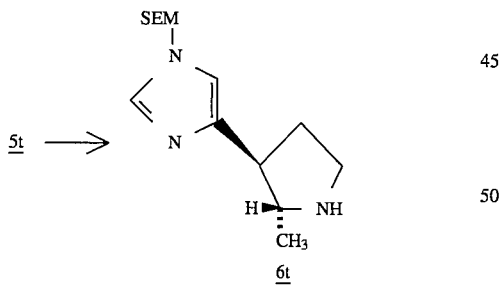

To a solution of the trans-lactam 5t (2.60 g, 8.8 mmol) in tetrahydrofuran (175 mL) was added a solution of lithium aluminum hydride in diethyl ether (1.0M, 44.0 mL, 44 mmol). The mixture was stirred at room temperature for 4 h and to the reaction mixture was added diethyl ether (440 mL) and saturated aqueous sodium sulfate (7 mL) dropwise. The mixture was dried over anhydrous sodium sulfate, filtered, and evaporated to give an oily residue which was purified by flash chromatography (gradient elution; CH$_2$Cl$_2$: MeOH/NH$_3$, 7:1 to 5:1) to give 6t as a colorless oil (1.15 g, 46%).

F. Preparation of pyrrolidine (6c)

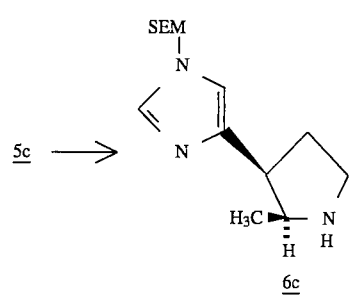

The cis-lactam 5c (0.60 g, 2.0 mmol) was treated in the same manner as described for the preparation of pyrrolidine 6t. The crude reaction product was purified by flash chromatography (gradient elution; CH$_2$Cl$_2$: MeOH/NH$_3$, 6:1 to 4:1) to give 6c as a colorless oil (0.36 g, 63%).

G. Preparation of ((±)-7t)

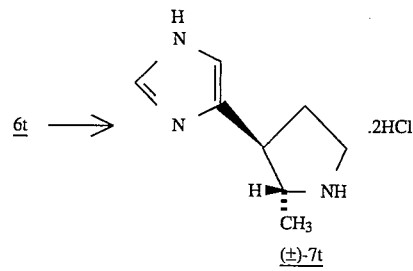

To a solution of the pyrrolidine 6t (563 mg, 2.0 mmol) in 95% ethanol (3 mL) was added concentrated hydrochloric acid (1mL) and the mixture was heated to reflux for 16 H. The solvents were removed by rotary evaporation and to the residue was added 1N aqueous hydrochloric acid (8 mL). This solution was extracted with ethyl acetate (3×4 mL) and the aqueous layer was concentrated by rotary evaporation. To the residue was added distilled water (15 mL) and the resulting solution was filtered through a glass wool plug. The filtrate was concentrated by rotary evaporation to give (±)-7t as a cream-colored solid (395 mg, 88%).

H. Purification of ((±)-7t)

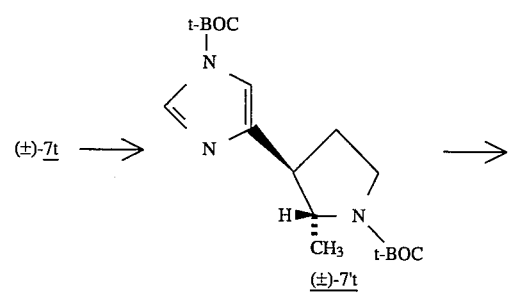

-continued

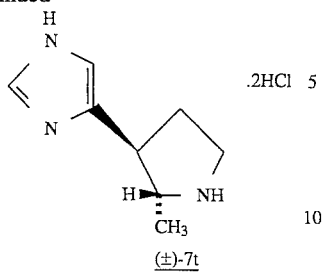

(±)-7t

To a solution of (±)-7t (336 mg, 1.5 mmol) in dimethylformamide (5.0 mL) was added triethylamine (1.05 mL, 7.53 mmol) and then a solution of di-tert-butyl dicarbonate (t-BOC)$_2$O (720 mg, 3.3 mmol) in dimethylformamide (1 mL). The mixture was stirred at room temperature for 2 h, the solvents were removed by vacuum distillation (2.0 mm Hg) and the resulting residue was purified by flash chromatography (gradient elution; EtOAc: hexane, 1:1 to 2:1) to give the corresponding di-t-BOC derivative (±)-7't (488 mg) as a white solid. This material was dissolved in ethyl acetate (3 mL), cooled to 5° C., and to this solution was added a saturation solution of hydrogen chloride in ethyl acetate (14 mL). The mixture was gradually warmed to room temperature (30 min) and stirred at this temperature for 16 h. The ethyl acetate was removed from the precipitated product by pipet and the precipitate was dried under high vacuum (0.1 mm Hg) to give (±)-7t as a white solid (286 mg, 85% recovery); MS(CI) 152 (M+1).

I. Resolution of ((±)-7t

The racemic (±)-7't was resolved by High Performance Liquid Chromatography using a Daicel Chiralcel OJ chiral chromatography column (2.0 cm×50.0 cm, 4% isopropanol in hexane). Multiple injections (13 injections of about 150 mg each) provided the levorotatory enantiomer (−)-7't:

950 mg; $[\alpha]_D^{26}$=−12.8°, c=0.50, CHCl$_3$, and the dextrorotatory enantiomer (+)-7't:

904 mg; $[\alpha]_{D\ hu\ 26}$=+12.0°, c=0.50, CHCl$_3$.

Treatment of (−)-7't with a saturation solution of hydrogen chloride in ethyl acetate as described above for the purification of (±)-7t provided (−)-7t:

$[\alpha]_D^{26}$=−34.6°, c=1.00, H$_2$O.

Similar treatment of (+)-7't gave (+)-7t:

$[\alpha]_D^{26}$=+39.4°, c=1.00, H$_2$O.

J. Preparation of ((±)-7c)

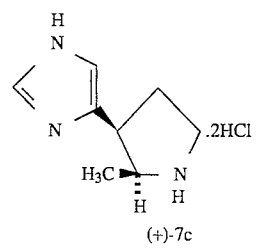

(+)-7c

The cis-pyrrolidine 6c (394 mg, 1.4 mmol) was treated as described for the preparation of (±)-7t to give (±)-7c as a cream-colored solid (288 mg, 95%). Compound (±)-7c (224 mg, 1.0 mmol) was purified as described for the purification of (±)-7t to give (±)-7c as a white solid (177 mg, 79% recovery); MS (CI) 152 (M+1).

Compounds 8, 9, 10t, 10c, 11t, 11c, 12t and 12c were prepared using the procedure described above for (±)-7t and 7c. The procedure is summarized below, A and B, and hence the compounds produced, are defined in Table 3.

K. Resolution of (±)-(7c)

In a manner similar to that described in Example 1, Steps H and I, racemic (±)-7c was resolved by High Performance Liquid Chromatography using a Daicel Chiralcel OD chiral chromatography column (5.0 cm×50.0 cm, 1% isopropaneol in hexane) followed by deprotection with a saturated solution of hydrogen chloride in ethyl acetate to give the levorotatory enantiomer (−)-7c:

$[\alpha]_D^{26}$=−35.7°, c=1.00, H$_2$O and the dextrorotatory enantiomer (+)-7c:

$[\alpha]_D^{26}$=+33.2°, c=1.00, H$_2$O.

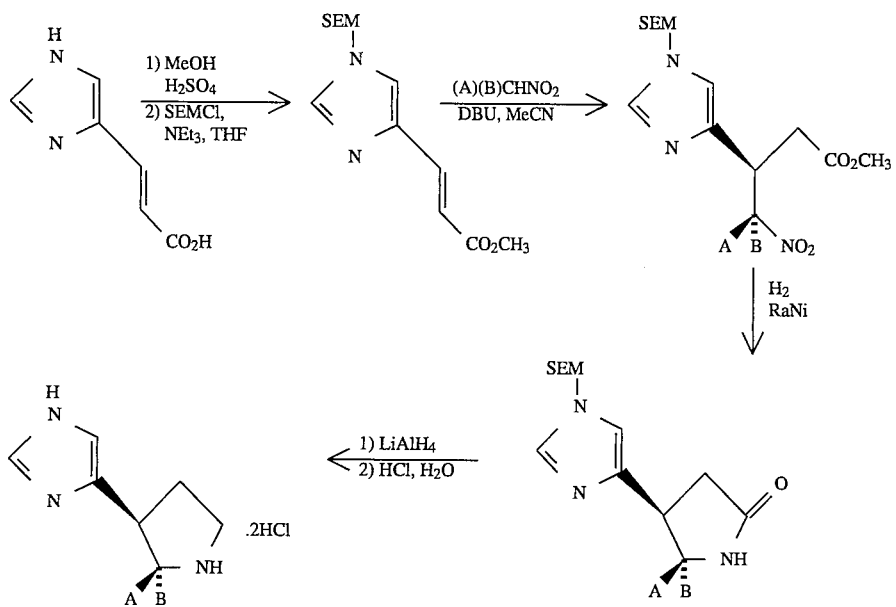

TABLE 3

| COMPOUND | A | B | MS(CI) (M + 1) |
|---|---|---|---|
| 8 | H | H | 138 |
| 9 | —CH₃ | —CH₃ | 166 |
| 10t | H | —CH₂CH₃ | 166 |
| 10c | —CH₂CH₃ | H | 166 |
| 11t | H | —CH₂C₆H₅ | 228 |
| 11c | —CH₂C₆H₅ | H | 228 |
| 12t | H | —CH₂CH₂C₆H₅ | 242 |
| 12c | —CH₂CH₂C₆H₅ | H | 242 |

EXAMPLE 2

A.

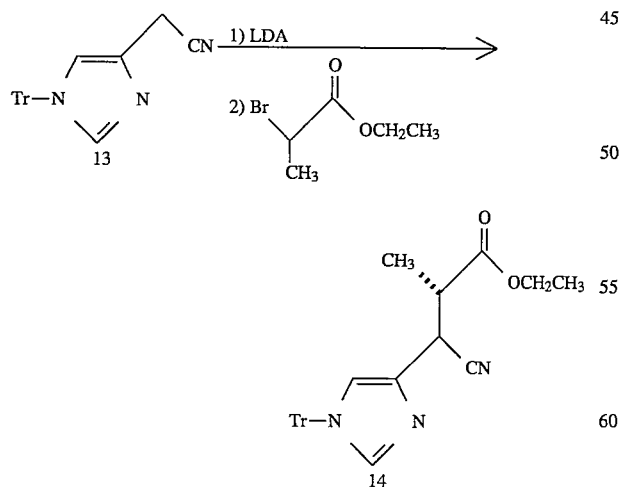

To a cooled (0° C.) solution of diisopropylamine (4 mmol, 561 μL) in dry THF (7 mL) was added n-BuLi (n-butyllithium) (2.5 mL of a 1.6M solution in hexane) dropwise. After 10 minutes at this temperature, the solution of LDA was cooled to −30° C. and a solution of 1 trityl-4-cyanomethyl imidazole 13 (4 mmol, 1.4 g, Tr=trityl)) in THF (6 mL) was added dropwise. After an additional 30 minutes at this temperature, a solution of ethyl-2-bromopropionate (4 mmol; 520 μL) in THF (5 mL) was added dropwise. The reaction was slowly warmed to RT (room temperature) (45 minutes) and quenched with 15 mL H₂O. The reaction was extracted with diethyl ether (3×25 mL) and the combined organic fractions were washed with brine, dried with MgSO₄, and filtered. Concentration of the rotovap yielded 1.65 g of an oil which was purified via column chromatography (75:25 hexane:ethyl acetate). 0.75 g (42%) of 14 was obtained as a mixture of diastereomers. MS (CI) 450 (M+1).

B.

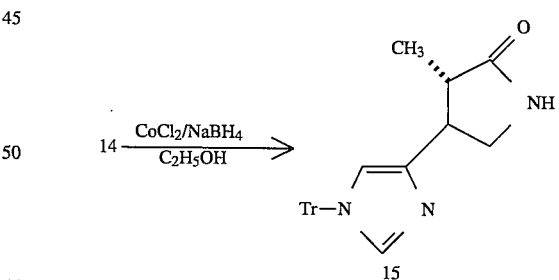

To a solution of 14 (6.23 mmol; 2.8 g) and CoCl₂.6 H₂O (6.23 mmol; 1.48 g) in absolute ethanol (150 mL) was added NaBH₄ (31.2 mmol; 1.18 g) portionwise over 30 minutes. After 4 hours, the black reaction mixture was concentrated to ⅓ the volume, shaken with ice-cold 3N HCl (50 mL) to dissolve the solids and rapidly basified to pH=9 was concentrated NH₄OH. The crude reaction was extracted with ethyl acetate (3×150 mL), the the combined organic layers were washed with brine, and dried (MgSO₄). Purification on a flash column (250 g SiO₂; 93:7 CH₂Cl₂: MeOH/NH₃) yielded 1.53 g (60%) of 15 as a white solid.

C.

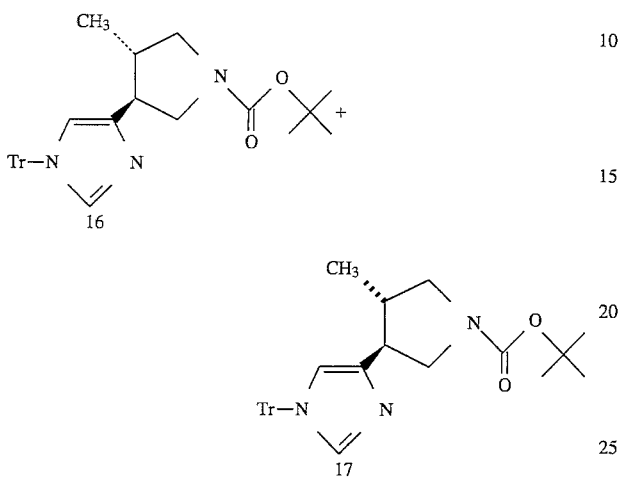

To a solution of lactam 15 (2.46 mmol; 1 g) in THF (30 mL) was added lithium aluminum hydride in diethyl ether (1M; 12.2 mL). The reaction was heated to 50° C. for 5.5 h, cooled to room temperature, diluted with diethyl ether, and quenched by careful dropwise addition of saturated aqueous $Na_2SO_4$. When $H_2$ evolution ceased, an additional 50 mL diethyl ether and solid $Na_2SO_4$ was added. The organic layer was filtered and concentrated to obtain 870 mg of a solid.

To a solution of the solid from the previous step in THF (20 mL) was added triethylamine (4.4 mmol; 614 μL) followed by di-t-butyl dicarbonate (2.75 mmol; 600 mg). After 2.5 h, brine was added and the reaction was extracted into EtOAc (100 mL). The combined organic layers were dried ($Na_2SO_4$), filtered, and concentrated. 600 mg (48%) of 16 and 660 mg (52%) of 17 were obtained after chromatography on a flash column (150 g $SiO_2$; 65:35 EtOAc:Hexane).

D.

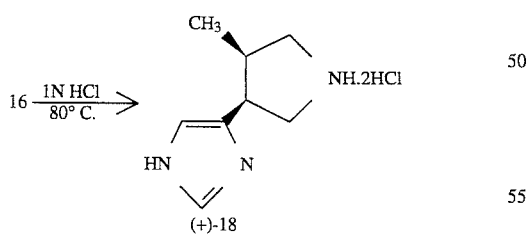

A suspension of 16 (1.2 mmol; 600 mg) in 1NHCl (30 mL) was heated to 80° C. for 1 hour. Compound 16 slowly dissolved and was replaced by a new solid. The reaction was cooled, filtered, and the aqueous layer was concentrated. Compound (±)-18, 170 mg, was obtained as a clear glass (64%) MS (EI) 151 ($M^+$).

In a similar manner, 17 yielded (±)-19 (175 mg, 60%) MS (EI) 151 ($M^+$).

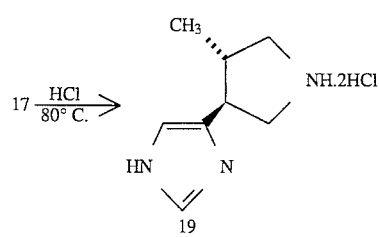

E. Resolution of (±)18 and (±)19

In a manner similar to that described in Example 1, Steps H and I, racemic (±)18 and (±)19 were resolved by High Performance Liquid Chromatography on a Chiralcel OD preparative column (2×50 cm) and gave after deprotection:

(+)-18 $[α]_D^{21.5}$=+37.6°, c=0.43, MeOH (−)-18 $[α]_D^{22}$=−32.2°, c=0.43, MeOH (+)-19 $[α]_D^{22}$=+39.0°, c=0.18, MeOH and (−)-19 $[α]_D^{22}$=−36.0°, c=0.20, MeOH.

By using the route described above for repairing (±)-18, the compounds listed in Table 4 were prepared:

TABLE 4

| STARTING MATERIAL | PRODUCT | MS |
|---|---|---|
| | | 166 (M + 1) (CI) |
| | | 207 (M⁺) (EI) |
| | | 207 (M⁺) (EI) |
| | | 166 (M + 1) (CI) |

EXAMPLE 3

A.

$15 \xrightarrow{\text{NaH}}_{\text{CH}_3\text{I}}$ 22

To a solution of 15 (1.4 mmol; 570 mg; see Step B of Example 2) in DMSO (10 mL) at room temperature was added NaH (1.4 mmol; 56 mg of a 60% dispersion in mineral oil). After 1.5 hours, CH₃I (1.4 mmol 87 μL) was added, and the reaction was stirred overnight. The reaction was diluted with H₂O and extracted into diethyl ether (3× 25 mL). The combined organic extracts were washed with brine, dried (Na₂SO₄), filtered, and concentrated. The crude product was purified on a flash column (100 g SiO₂; 95:5 CH₂Cl₂: CH₃OH/NH₃). Compound 22, 290 mg (49%), was obtained.

B.

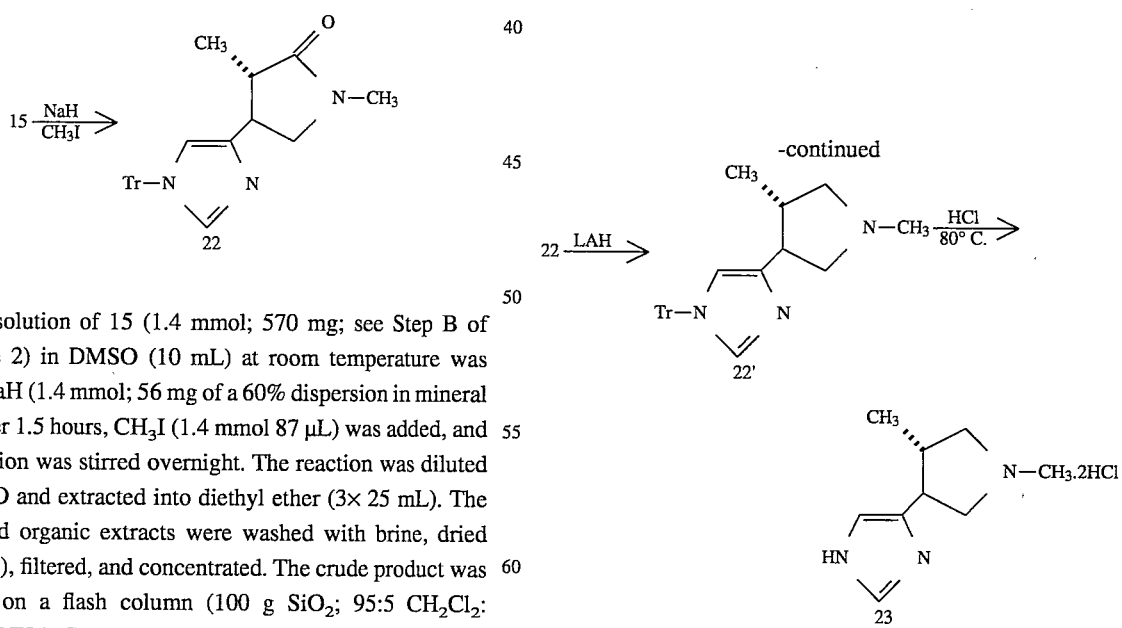

$22 \xrightarrow{\text{LAH}}$ 22'  $\xrightarrow{\text{HCl}}_{80° \text{C.}}$ 23

By using the route described in Example 2, Steps C and D, compound 22 was converted to 23 (62 mg, 67%); MS(CI) 166(M+1).

EXAMPLE 4

A. Preparation of α-methyl-nitrile (24)

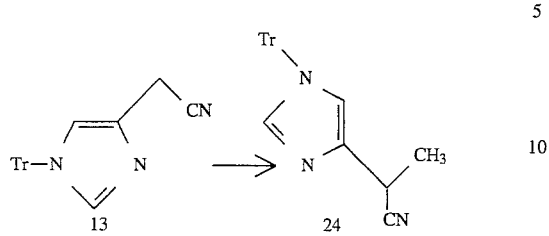

To a solution of diisopropylamine (0.775 mL, 5.5 mmol) in tetrahydrofuran (15 mL) at −78° C. was added a solution of n-butyllithium in hexane (2.5 M, 2.1 mL, 5.25 mmol) and the mixture was stirred at −78° C. for 1 h. To this was added a solution of the nitrile 13 (1.75 g, 5.0 mmol, see Step A of Example 2) in tetrahydrofuran (10 mL) and the mixture was stirred at −78° C. for 1 h. To this solution was added a solution of methyl iodide (325 μL, 5.2 mmol) in tetrahydrofuran (2.5 mL), the mixture was stirred at −78° C. for 30 min and then warmed to 0° C. (1 h). To the mixture was added saturated aqueous ammonium chloride (2 mL), the solvents were removed by rotary evaporation and to the residue was added methylene chloride (200 mL), water (25 mL) and saturated aqueous sodium bicarbonate (25 mL). The mixture was shaken vigorously, the layers separated and the organic layer was dried over anhydrous sodium sulfate, filtered and evaporated to give a yellow solid residue. This crude product was purified by flash chromatography (hexane:isopropanol, 4:1) to give the α-methyl-nitrile 24 as an off-white solid (1.33 g, 73%).

B. Preparation of nitrile-ester (25)

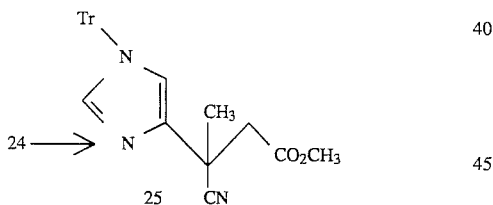

To a solution of diisopropylamine (0.550 mL, 3.9 mmol) in tetrahydrofuran (12 mL) at −78° C. was added a solution of n-butyllithium in hexane (2.5 M, 1.50 mL, 3.75 mmol) and the mixture was stirred at −78° C. for 1 h. To this was added a solution of the α-methyl-nitrile 24 (1.27 g, 3.5 mmol) in tetrahydrofuran (10 mL) and the mixture was stirred at −78° C. for 1 h. To this solution was added a solution of ethyl bromoacetate (420 μL, 3.79 mmol) in tetrahydrofuran (2.0 mL), the mixture was stirred at −78° C. for 1 h and then warmed to 0° C. (1 h). To the mixture was added saturated aqueous ammonium chloride (1.5 mL), the solvents were removed by rotary evaporation and to the residue was added methylene chloride (200 mL) and saturated aqueous sodium chloride (40 mL). The mixture was shaken vigorously, the layers separated and the organic layer was dried over anhydrous sodium sulfate, filtered and evaporated to give a yellow oily residue. This crude product was purified by flash chromatography (hexane:acetone, 3:1 to 2:1) to give the nitrile-ester 25 as a colorless glass (1.44 g, 90%).

C. Preparation of Lactam (26)

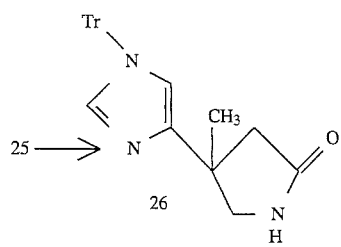

To a solution of the nitrile-ester 25 (1.39 g, 3.1 mmol) in absolute ethanol (70 mL) was added a solution of cobalt dichloride hexahydrate (736 mg, 3.1 mmol) in absolute ethanol (10 mL) and then portionwise (5 min) sodium borohydride (700 mg, 18.5 mmol). The mixture was stirred at room temperature for 2 h, the solvents were removed by rotary evaporation and to the black residue was added color (5° C.) 3M aqueous hydrochloric acid (34 mL). The mixture was shaken until the black precipitate dissolved (5 min) and then to this mixture was added concentrated ammonium hydroxide (10 mL). This solution was extracted with ethyl acetate (2×250 mL) and the combined organic layers were dried over anhydrous sodium sulfate, filtered and evaporated to give an off-white solid residue which was purified by flash chromatography (gradient elution: 8% to 10% $CH_3OH/NH_3$ in $CH_2Cl_2$) to give the lactam 26 as a white solid (1.05 g, 83%).

D. Preparation of the Pyrrolidine (27)

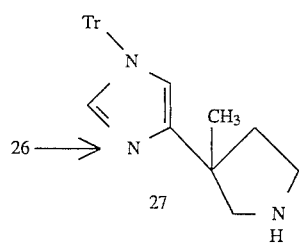

The lactam 26 (1.05 g, 2.58 mmol) was treated with a solution of lithium aluminum hydride in diethyl ether (1.0 M, 13.0 mL, 13.0 mmol) as described for the preparation of the pyrrolidine 6t (see Example 1, Step E). The crude product was purified by flash chromatography (gradient elution: $CH_2CL_2$: $CH_3OH/NH_3$, 8:1 to 7:1 to 6:1) to give the pyrrolidine 27 as a colorless glass (720 mg, 71%).

E. Preparation of Compound (28)

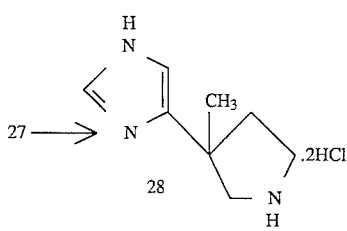

A suspension of the pyrrolidine 27 (750 mg, 1.91 mmol) in 1N aqueous hydrochloric acid (15 mL) was heated to reflux for 1 h. The white precipitate that formed during the course of the reaction was removed by filtration and the aqueous filtrate was extracted with ethyl acetate (2×5 mL). The aqueous layer was concentrated by rotary evaporation to give compound 28 as an off-white solid (390 mg, 91%).

F. Purification of Compound (28)

Compound 28 (75 mg, 0.33 mmol) was purified as described for the purification of Compound (±)-7t (see Example 1, Step H) to give Compound 28 as a white solid (57 mg, 76% recovery); MS (CI) 152(M+1).

A.

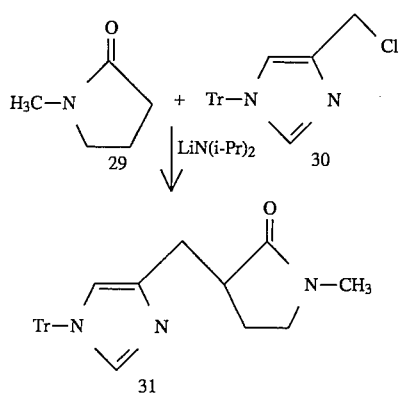

EXAMPLE 5

To a solution of 1.08 mL of freshly distilled N,N-diisopropylamine in 1 mL of anhydrous THF was added 3.1 mL of 2.5 M n-butyllithium at 0° C. under nitrogen. The resulting solution was stirred at 0° C. for 40 minutes (resulting in the production of lithium diisopropylamide (LiN(i-Pr)₂)), cooled to −23° C. and then 0.672 mL of N-methyl- 2-pyrrolidinone 29 was added slowly. The solution was stirred for 0.5 hours at −23° C. and an additional 1 hour at −78° C. A solution of 2.69 g of 4-chloromethyl-(N-trityl)imidazole 30 in 14 mL of anhydrous THF was then added dropwise. The resulting solution was stirred for 4 hours at −78° C. and slowly warmed to room temperature. After a couple of hours at −78° C. and slowly warmed to room temperature. After a couple of hours of stirring at room temperature, the reaction mixture was quenched by water and extracted with ethyl acetate. The combined organic extracts were washed with brine, dried over anhydrous MgSO₄ and concentrated to give crude product. The crude product was purified by flash chromatography on SiO₂ (1% to about 5% of ammonia saturated methanol in CH₂Cl₂) to give 1.77 (60% yield) of compound 31.

B.

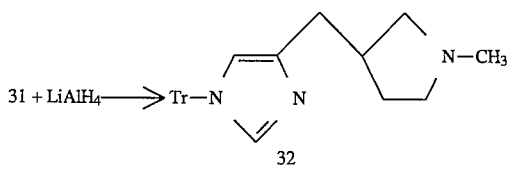

To a solution of 1.54 g of 31 in 8 mL of anhydrous THF was added 11.34 mL of lithium aluminum hydride solution (1.0M in diethyl ether) slowly. The resulting solution was stirred at room temperature for 2 hours, and 110 mL of diethyl ether was added. Saturated aqueous Na₂SO₄ solution was carefully added to the above mixture till hydrogen evolution ceased. The organic fraction was separated, and the aqueous solution was basified with K₂CO₃ and extracted with ethyl acetate many times. The combined organic solutions were washed with brine, dried over anhydrous K₂CO₃, and then concentrated to give a crude product. The crude product was purified by flash chromatography on SiO₂ (5% CH₃OH(NH₃) in CH₂Cl₂) to give 1.273 g (85% yield) of compound 32.

C.

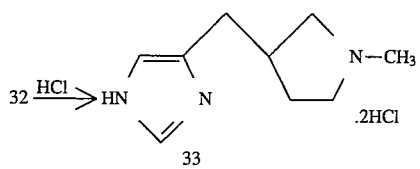

A solution of 1.2 g of 32 in 100 mL of 0.5N aqueous hydrochloric acid was heated in a 90° C. oil bath for 30 minutes. After the solution was cooled to room temperature, the mixture was extracted with diethyl ether (4×50 mL). The aqueous solution was concentrated under vacuum to yield crude product which was then recrystallized from 2-propanol/diethyl ether to give 0.5 g (85%) of compound 33; MS (FAB) 166(M+1).

EXAMPLE 6

A.

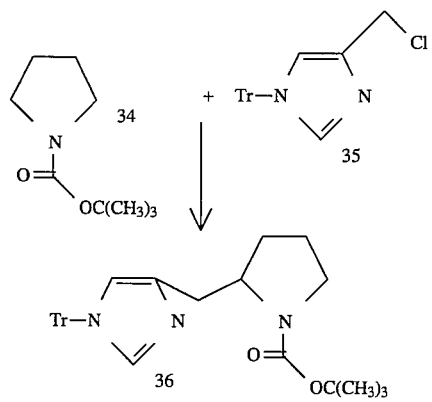

To a solution of 1.194 g of compound of formula 34 and 2.49 mL of tetramethyethylenediamine in 7.5 ml of anhydrous diethyl ether was added 6.06 ml of 1.3N sec-butyllithium at −78° C. The resulting solution was stirred for 3 hours 45 minutes at −78° C., and a solution of 1.9074 g of chloromethyl (N-trityl)imidazole 35 in 4 ml of tetrahydrofuran was added dropwise over 15 minutes. After 15 minutes of stirring at −78° C., the reaction mixture was slowly warmed to room temperature for over 1 hour. Saturated aqueous NH₄Cl solution was added. The mixture was extracted with ethyl acetate. The organic layer was separated, washed with brine, dried over anhydrous sodium sulfate and then concentrated. The residue was purified by flash chromatography on SiO₂ to give 0.23 g (17%) of product 36.

B.

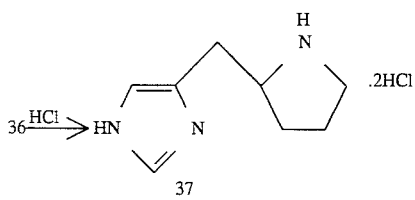

A solution of 0.23 g of 36 in 20 mL of 0.5N HCl was heated to reflux for 45 minutes. After cooling to room temperature, the mixture was extracted with diethyl ether three times. The aqueous solution was then concentrated and the crude product was crystallized with $CH_3OH$/diethyl ether to give 0.75 g (70% yield) of the product 37; MS (CI)152 (M+1).

EXAMPLE 7

A.

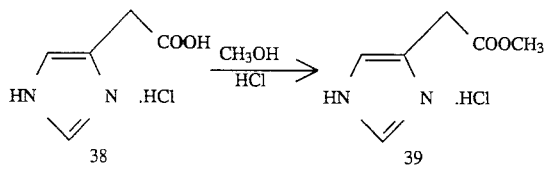

To a solution of 11.59 g of imidazole acetic acid hydrochloride 38 in 100 mL of anhydrous methane was added 1 mL of concentrated HCl. The resulting mixture was refluxed for 5.5 hours, and then cooled to room temperature. After concentration of the solvent, 11.9 g (95%) of the product 39 was isolated.

B.

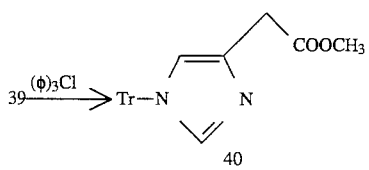

To a solution of 7.8 g of 39 in 70 mL of anhydrous DMF at 0° C. was added 12.94 g of trityl chloride $((\phi)_3Cl)$ and 18.4 mL of triethyl amine. The resulting solution was stirred at room temperature for 24 hours, and the solvent was removed under vacuum. The residue was purified by flash chromatography on $SiO_2$(eluting solvent: $CH_2Cl_2$ and increase polarity slowly by addition of ethyl acetate) to give 16.1 g of product 40 (95% yield).

C.

-continued

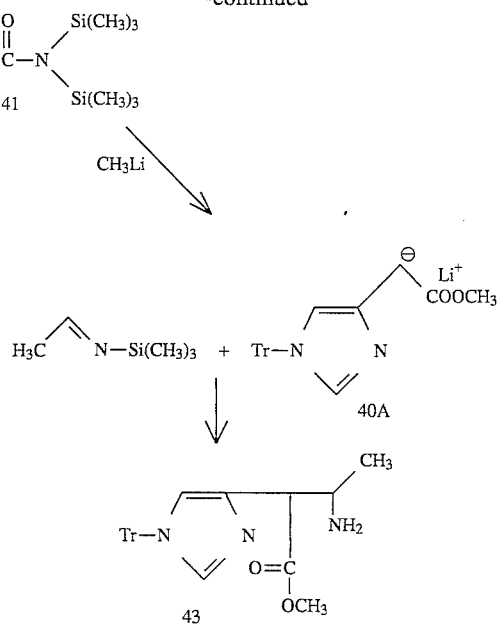

To a solution of 8.15 mL of compound 41 in 50 mL of anhydrous THF was added 26.25 mL of 1.4M methyllithium at −78° C. The above solution was stirred for 1 hour at −78° C. and a solution of 40A (prepared by the addition of 25 mL of 1M $LiN(Si(CH_3)_3)_2$ to a solution of 9.55 g of 40 in 100 mL of anhydrous THF at −78° C. and stirring the solution for 2 hours at −78° C. before transferring) was added by cannula over 30 minutes. Ten minutes later, 4.6 mL of $BF_3.(C_2H_5)_2O$ was added to the above mixture, and the resulting solution was stirred at −78° C. for 2 hours. The reaction mixture was slowly warmed up to room temperature (over 2 hours 45 minutes), and then saturated aqueous $naHCO_3$ solution was added. The organic layer was separated and the aqueous layer was extracted with EtOAc. The organic layer and EtOAc extracts were combined and the combined organic solution was washed with brine, dried over $MgSO_4$ and then concentrated. The residue was purified by flash chromatography (silica gel was deactivated with triethylamine, eluting solvent: 1 to 10% of $CH_3OH$ in EtOAc) to give compound 43 (6.4 g; 60% yield).

D.

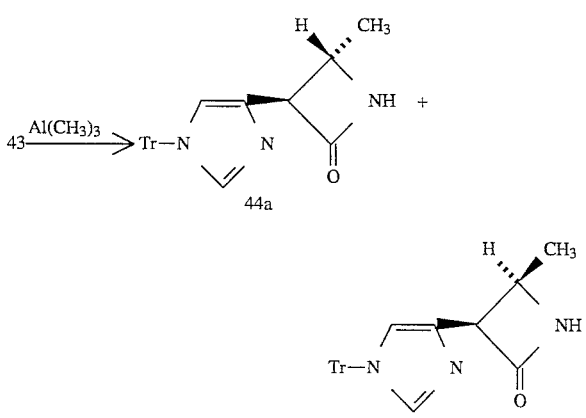

To a solution of 6.4 g of 43 in 250 mL of anhydrous methylene chloride was added 11.3 mL of 2.0M trimethyl aluminum. The resulting mixture was stirred at room temperature for 45 minutes, heated to reflux (5 hours), cooled to 0° C., and to this mixture was added saturated aqueous NaHCO₃ solution. The organic layer was separated, washed with brine, dried over Na₂SO₄ and concentrated. The residue was purified by flash chromatography (silica gel deactivated with triethylamine; eluting solvent EtOAc to 1 to about 2% CH₃OH in EtOAc) to give 0.91 g of 44a (trans isomer) and 0.39 g of 44b (cis isomer).

E.

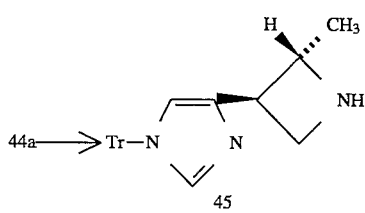

To a solution of 0.3225 g of 44a in 8 mL of anhydrous THF was added 3.28 mL of 1M solution of diisobutylaluminium hydride in toluene dropwise at room temperature. After the addition was complete, the solution was refluxed for 2 hours and cooled to room temperature. Water (2 mL) was added slowly to the above solution and 20 ml of methylene chloride was added to the resulting mixture. The mixture was vigorously stirred until a white solid precipitated out. Filtration and concentration gave crude product, which was purified by preparative TLC (deactivated with triethylamine; eluting solvent 7.5% CH₃OH in CH₂Cl₂) to give 0.187 g (60% yield) of 45.

F.

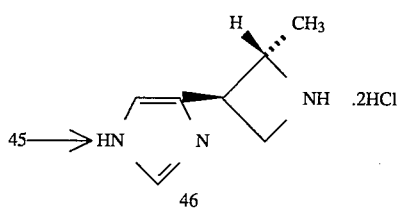

A solution of 0.148 g of 45 in 12 mL of 0.5N HCl was heated in an oil bath at 90° C. for 0.5 hours. The solution was then cooled to room temperature. The mixture was extracted with diethyl ether three times, and the aqueous solution was concentrated to give a crude product. The crude product was recrystallized in CH₃OH/diethyl ether to give 70 mg (85%) of 46; MS(CI) 138 (M+1).

By following the procedures set forth in Example 7, Steps E and F, compound 44b can be converted to the cis isomer of 46.

EXAMPLE 8

A.

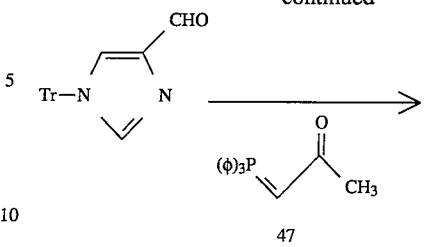

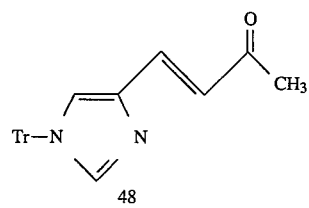

A mixture of 9.78 g of 4-(N-tritylimidazoyl)carboxaldehyde and 9.55 g of Wittig reagent 47 in 30 mL of anhydrous THF was refluxed for 21 hours. An additional 4.8 g of Wittig reagent 47 and 10 mL of THF were added to the above mixture; the resulting mixture was continually refluxed for 30 hours. The solvent was concentrated. The residue was dissolved in CH₂Cl₂ and washed with water. The organic layer was separated and concentrated. The residue was purified by flash chromatography on SiO₂(CH₂Cl₂/EtOAc) to give 6.14 g (81% yield) of 48.

B.

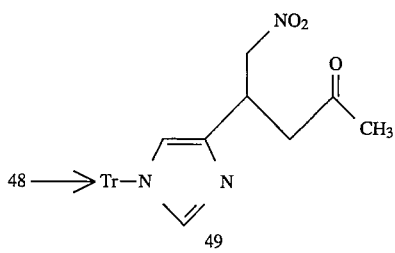

To a mixture of 4.5 g of ketone 48 in 18 mL of CH₃CN was added 6.62 mL of nitromethane and 75 mL of THF. To the above homogenous solution was added 1.835 mL of DBU (1,8-diazabicyclo[ 5.4.0]undec-7-ene) and the resulting solution was stirred at room temperature overnight (18 hours). The reaction mixture was poured into ice cold 01N HCl solution and the mixture was extracted with EtOAc. The combined EtOAc extracts were washed with brine, dried over MgSO₄ and concentrated to give 4.54 g (87%) of product 49.

C.

-continued

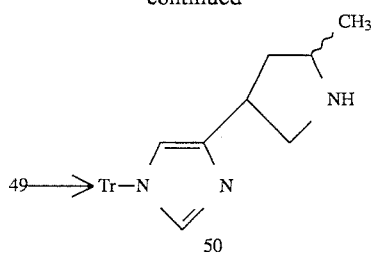

Compound 49 was reduced by mixing 1.5 g of 49, 1.5 g of Raney-Ni and 1.5 g of anhydrous Na$_2$SO$_4$ in 50 mL of absolute ethanol and subjecting the resulting mixture to 60 psi. of H$_2$ for 26 hours. The reaction mixture was filtered through a pad of celite and the pad was washed with ethanol and CH$_2$Cl$_2$. The filtrate was concentrated to yield 0.83 g of 50 (62%).

D.

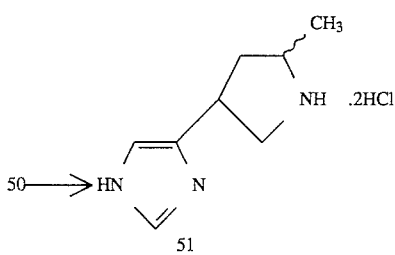

A solution of 0.83 g of 50 in 30 mL of 0.5N HCl was heated to reflux for 45 minutes. After the mixture was cooled to room temperature, it was extracted with diethyl ether. The aqueous layer was evaporated to dryness to give 0.43 g of crude product 51.

E.

51 $\xrightarrow{(tBOC)_2O}$

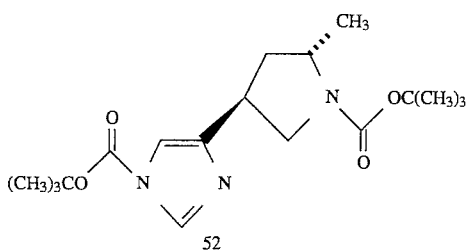

To a mixture of 0.34 g of 51 in 5 mL of anhydrous DMF was added 1.69 mL of triethylamine; the mixture was stirred for 5 minutes and 0.77 mL of di-tert-butyldicarbonate ((tBOC)$_2$O)was added. The reaction mixture was stirred for 18 hours at room temperature, filtered and concentrated. The residue was dissolved in water and extracted with EtOAc. The combined organic extracts were washed with brine, dried over anhydrous Na$_2$SO$_4$ and concentrated. The residue was purified by preparative TLC (1:1 EtOAc/hexane) to give 0.13 g (24% yield) of 52; MS (M/e) 352 (M+1).

F.

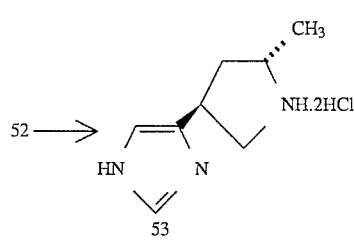

A solution of 0.13 g of 52 in 6 mL of EtOAc (saturated with HCl) was stirred for 45 minutes at 0° C., then the solvent was evaporated under vacuum. The residue was recrystallized in 2-propanol/diethyl ether to give 0.067 (81% yield) of 53; MS(SI) 152(M+1).

EXAMPLE 9

A.

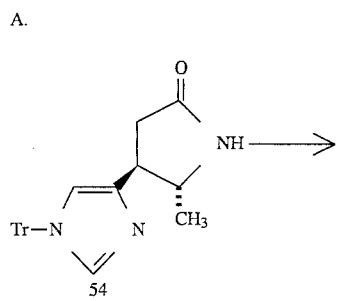

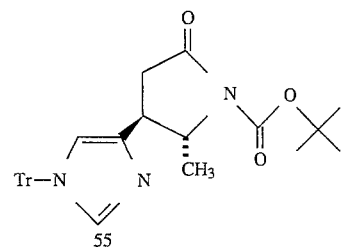

To a solution of lactam 54 (10 mmole; 4.07 g) (synthesized in a manner similar to 5t) in dry THF (55 mL) at −78° C. was added a solution of LDA (11 mmol, 1.18 g) in THF (15 mL). After 45 minutes at this temperature, the reaction was warmed to room temperature for 20 minutes and then recooled to −78° C. A solution of (tBOC)$_2$O (11 mmol, 2.41 g) in THF (15 mL) was added and the reaction was slowly warmed to room temperature. The reaction was then quenched with water and extracted into diethyl ether. The combined ether extracts were washed with brine and dried (MgSO$_4$). Concentration yielded a solid that was recrystallized from hexane: 2-propanol. Compound 55, 3.5 g (69%), was obtained as an off-white solid.

B.

-continued

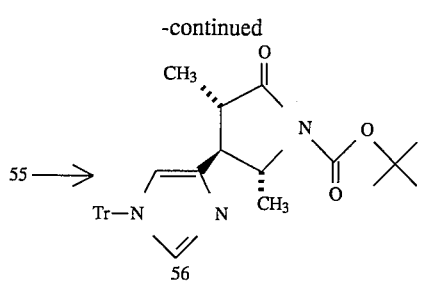

To a solution of 55 (6.9 mmol, 3.5 g) in dry THF (50 mL) at −78° C. was added a solution of KN(Si(CH₃)₃)₂ (8.63 mmol, 1.72 g) in THF (20 mL) over 10 minutes. An additional 10 mL THF was used to rinse the flask and syringe. After one hour at −78° C., neat CH₃I (8.63 mmol, 1.22 g, filtered through basic alumina) was added, and the reaction was warmed to room temperature. After 2.5 hours, the reaction was recooled to −78° C., quenched and saturated NH₄Cl (pH=7.3) and extracted into diethyl ether. The combined ether extracts were washed with brine and dried (MgSO₄). Concentration and purification via flash column chromatography (400 g SiO₂; 90:10 hexane: 2-propanol) yielded 56 (2.35 g; 65%).

C.

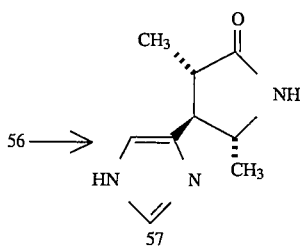

To a solution of 56 (4.2 mmol, 2.19 g) in dry CHCl₃ (40 mL) at room temperature was added iodotrimethylsilane (10.51 mmol, 2.1 g). After one hour at 40° C., the reaction was diluted with methanol and concentrated on the rotary evaporator. Purification via flash chromatography (150 g, SiO₂, 80:10:10 CH₂Cl₂:2-propanol: methanol/ammonia) gave 600 mg (80%) of 57.

D.

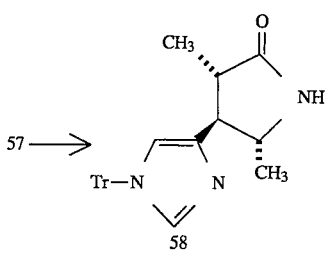

Compound 57 (3.6 mmol, 640 mg) was combined with trityl chloride (3.9 mmol, 1.48 g) and triethylamine (3.9 mmol, 0.39 g) in dry CH₂Cl₂ (25 mL) at room temperature under nitrogen. After 6 hours, the reaction was quenched with water and extracted with EtOAc/CH₂Cl₂ (4:1)(EtOAc represents ethyl acetate). The combined organic layers were washed with saturated aqueous sodium metabisulfite and dried (MgSO₄). The crude material was purified on a flash column (175 g SiO₂, 95:5 CH₂Cl₂: methanol/ammonia) and yielded 900 mg (59%) of 58.

E.

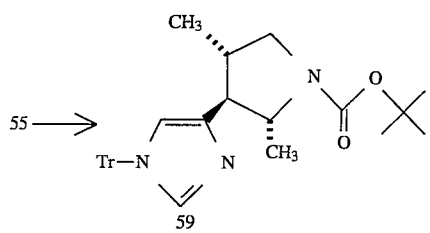

To a solution of 58 (2.14 mmol, 900 mg) in dry THF (30 mL) was added a solution of LAH in diethyl ether (5.34 mL of a 1M solution). The reaction was heated to reflux for 2 hours, cooled to room temperature, diluted with diethyl ether, and quenched with saturated aqueous Na₂SO₃. Solid Na₂SO₄ was added and the mixture was filtered. The filter cake was washed with 150 mL of boiling THF. Removal of the solvent on the rotary evaporator yielded 920 mg of a crude solid.

To a solution of the crude solid (920 mg) from the previous reaction in THF (15 mL) was added (t-BOC)₂O (2.7 mmol, 0.59 g). After 30 minutes, the reaction was diluted with CH₂Cl₂, washed with water, and dried (MgSO₄). Concentration yielded a crude solid which was purified on a flash column (200 g SiO₂, 80:20 hexane:acetone). This material was further purified via HPLC (SiO₂, 97:3 hexane:2-propanol) to give 230 mg (21%) of 59.

F.

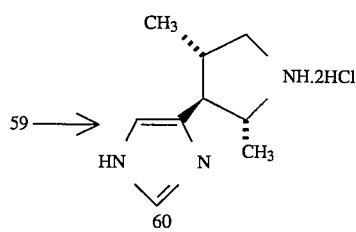

Compound 59 (0.47 mmol, 230 mg) was combined with 15 mL 1N HCl and heated to 90° C. for one hour. The reaction was cooled, filtered, and extracted with diethyl ether. The aqueous layer was concentrated in vacuo to give 60 (110 mg, 100%). MS(CI) 166 (M+1).

The following are examples of pharmaceutical dosage forms which contain a compound of the invention. As used therein, the term "active compound" is used to designate the compound

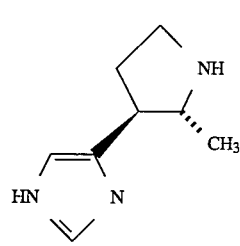

The scope of the invention in its pharmaceutical composition aspect is not to be limited by the examples provided, since any other compound of structural formula I can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method of Manufacture

Mix Items Nos. 1 and 2 in a suitable mixer for 10–15 minutes. Granulate the mixture with Item No. 3. Mill the damp granules through a coarse screen (e.g., ¼"0.63 cm) if necessary. Dry the damp granules. Screen the dried granules if necessary and mix with item No. 4 and mix for 10–15 minutes. Add Item No. 5 and mix for 1–3 minutes. Compress the mixture to appropriate size and weigh on a suitable tablet machine.

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
|  | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

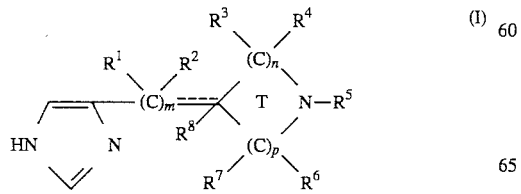

or a pharmaceutically acceptable salt or solvate thereof, wherein:

(A) m is an integer selected from the group consisting of: 0, 1, and 2;

(B) n and p are integers and are each independently selected from the group consisting of: 0, 1, 2, and 3 such that the sum of n and p is 2 or 3 such that when the sum of n and p is 2, T is a 4-membered ring and when the sum of n and p is 3, T is a 5-membered ring;

(C) each $R^1$, $R^2$, $R^3$, $R^4$, $R^6$, $R^7$, and $R^8$ is independently selected from the group consisting of:
  (1) H;
  (2) $C_1$ to $C_6$ alkyl;
  (3) $C_3$ to $C_6$ cycloalkyl; and
  (4) —$(CH_2)_q$—$R^9$ wherein q is an integer of: 1 to 7, and $R^9$ is selected from the group consisting of: phenyl, substituted phenyl, —$OR^{10}$, —$C(O)OR^{10}$, —$C(O)R^{10}$, —$OC(O)R^{10}$, —$C(O)NR^{10}R^{11}$, CN and —$SR^{10}$ wherein $R^{10}$ and $R^{11}$ are as defined below, and wherein the substituents on said substituted phenyl are each independently selected from the group consisting of: —OH, —O—($C_1$ to $C_6$)alkyl, halogen, $C_1$ to $C_6$ alkyl, —$CF_3$, —CN, and —$NO_2$, and wherein said substituted phenyl contains from 1 to 3 substituents;

(D) $R^5$ is selected from the group consisting of:
  (1) H;
  (2) $C_1$ to $C_{20}$ alkyl;
  (3) $C_3$ to $C_6$ cycloalkyl;
  (4) —$C(O)OR^{10'}$; wherein $R^{10'}$ is the same as $R^{10}$ defined below except that $R^{10'}$ is not H;
  (5) —$C(O)R^{10}$;
  (6) —$C(O)NR^{10}R^{11}$;
  (7) allyl;
  (8) propargyl; and
  (9) —$(CH_2)_q$—$R^9$, wherein q and $R^9$ are as defined above with the proviso that when q is 1 then $R^9$ is not —OH or —SH;

(E) $R^{10}$ and $R^{11}$ are each independently selected from the group consisting of: H, $C_1$ to $C_6$ alkyl, and $C_3$ to $C_6$ cycloalkyl; and, for the substituent —$C(O)NR^{10}R^{11}$, $R^{10}$ and $R^{11}$, together with the nitrogen to which they are bound, can form a ring having 5, 6, or 7 atoms;

(F) the dotted line ( ... ) represents a double bond that is optionally present when m is 1, and T is a 5-membered ring, and n is not 0, and p is not 0, and when said double bond is present then $R^2$ and $R^8$ are absent;

(G) when m is 2, each $R^1$ is the same or different substituent for each m, and each $R^2$ is the same or different substituent for each m;

(H) when n is 2 or 3, each $R^3$ is the same or different substituent for each n, and each $R^4$ is the same or different substituent for each n; and (I) when p is 2 or 3, each $R^6$ is the same or different substituent for each p, and each $R^7$ is the same or different substituent for each p.

2. The compound of claim 1 wherein said compound is selected from the group consisting of compounds having the formula:

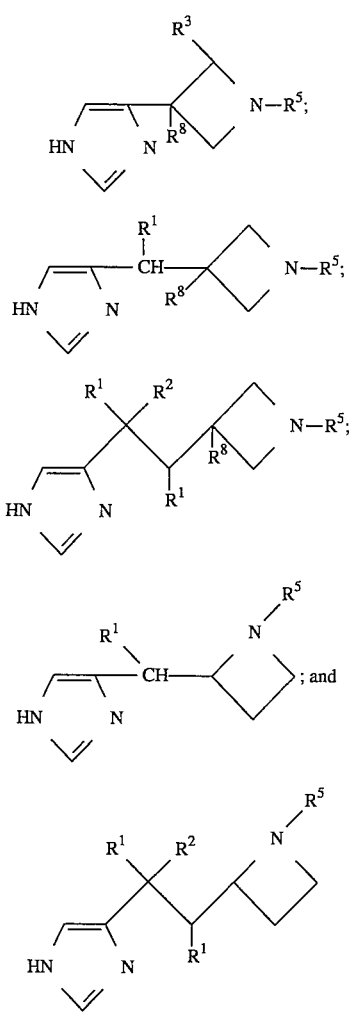

wherein $R^1$, $R^2$, $R^3$, $R^4$, and $R^8$ are as defined for Formula I.

3. The compound of claim 1 wherein said compound is selected from the group consisting of compounds having the formula:

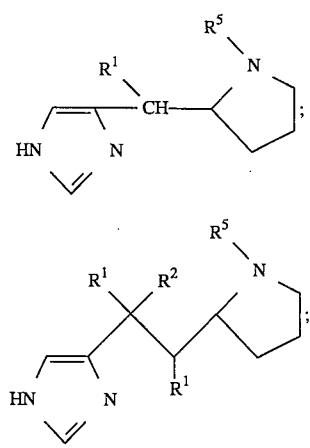

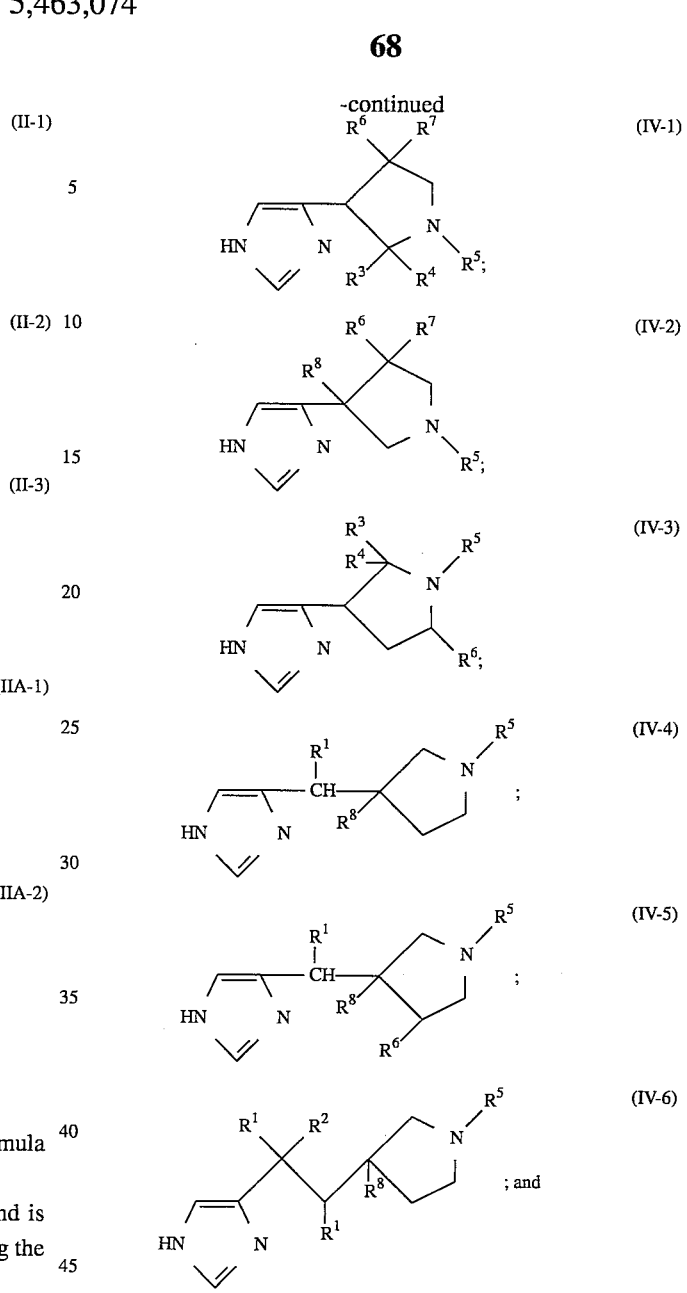

wherein $R^1$, $R^2$, $R^3$, $R^4$, $R^5$, $R^6$, $R^7$, and $R^8$ are as defined for Formula I.

4. The compound of claim 1 wherein m is 0 or 1.

5. The compound of claim 4 wherein $R^5$ is selected from the group consisting of H, $C_1$ to $C_{20}$ alkyl and $(CH_2)_q$—$R^9$ wherein $R^9$ is phenyl.

6. The compound of claim 5 wherein $R^1$ to $R^4$ and $R^6$ to $R^8$ are each independently selected from the group consisting of H, $C_1$ to $C_6$ alkyl, and —$(CH_2)_q$—$R^9$ wherein $R^9$ is phenyl.

7. The compound of claim 6 wherein each $R^1$ to $R^4$ and $R^6$ to $R^8$ are independently selected from the group consisting of H, methyl, ethyl, pentyl, benzyl, and 2-phenylethyl.

8. The compound of claim 7 wherein $R^5$ is H or methyl.

9. The compound of claim 1 having the formula selected from the group consisting of:

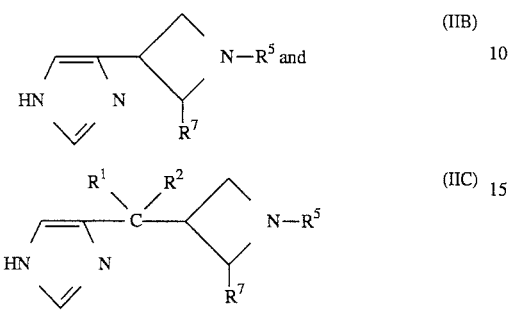

wherein $R^7$ is selected from the group consisting of H, $C_1$ to $C_6$ alkyl, and $-(CH_2)_q-R^9$ wherein $R^9$ is phenyl.

10. The compound of claim 9 wherein $R^7$ is $C_1$ to $C_6$ alkyl, $R^1$ is H, and $R^2$ is H.

11. The compound of claim 1 having the formula selected from the group consisting of:

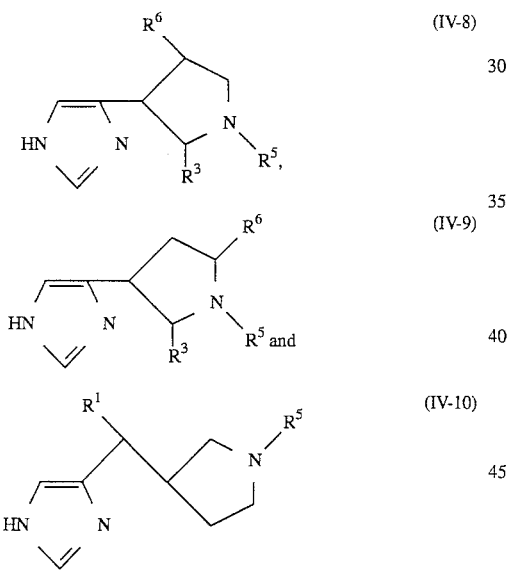

wherein $R^1$, $R^3$ and $R^6$ are each independently selected from the group consisting of H, $C_1$ to $C_6$ alkyl and $-(CH_2)_q-R^9$ wherein $R^9$ is phenyl.

12. The compound of claim 11 wherein $R^5$ is selected from the group consisting of H and methyl.

13. The compound of claim 12 wherein $R^1$ is H.

14. The compound of claim 1 wherein said compound is selected from the group consisting of:

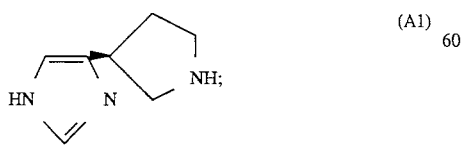

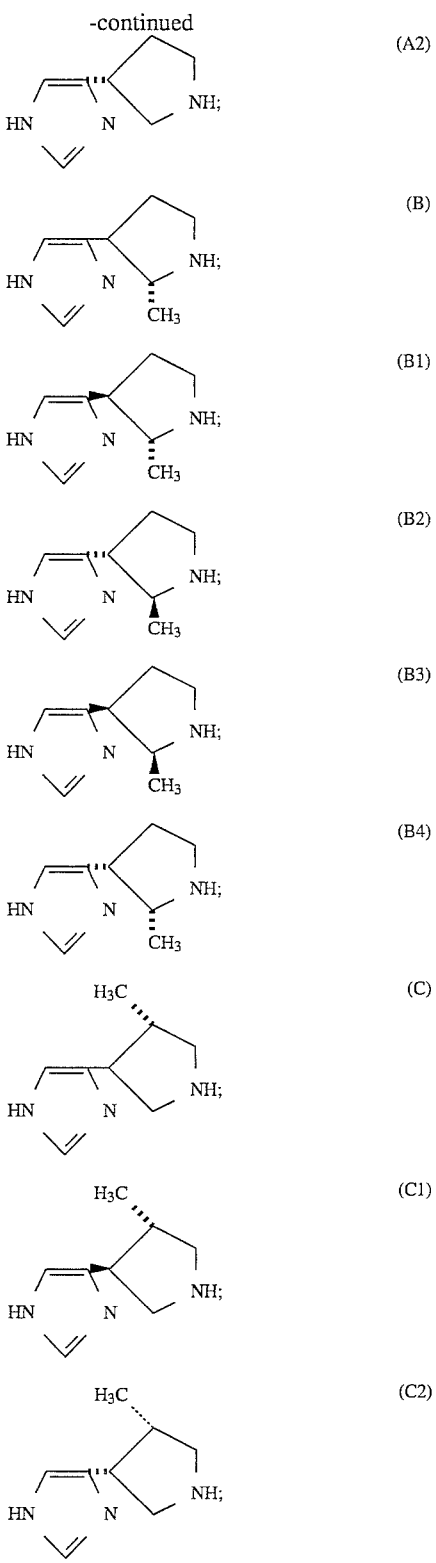

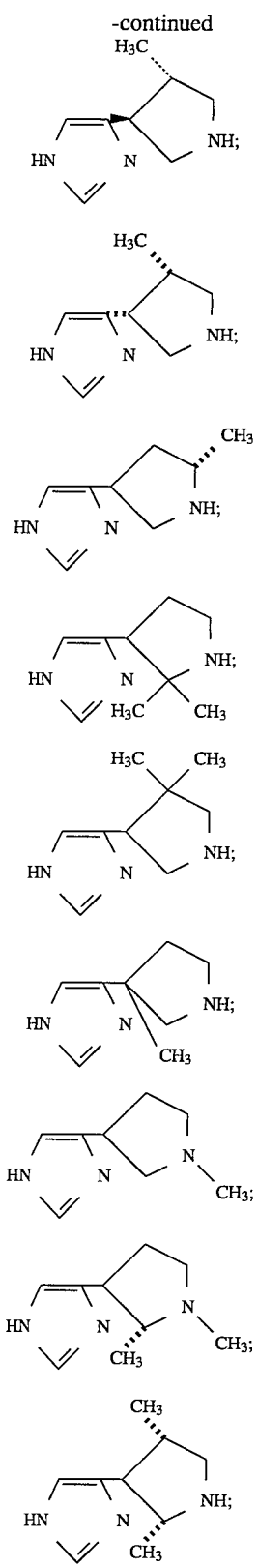
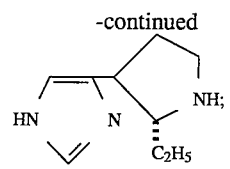

15. The compound of claim 14 having the formula:

(B1)

16. The compound of claim 14 having the formula:

(B2)

17. The compound of claim 14 having the formula:

(C1)

18. The compound of claim 14 having the formula:

(C2)

19. A pharmaceutical composition comprising a pharmaceutically acceptable carrier and an effective amount of a Compound of claim 1.

* * * * *